(12) United States Patent
Jung et al.

(10) Patent No.: US 9,168,114 B2
(45) Date of Patent: *Oct. 27, 2015

(54) METHOD OF MAKING A DENTAL PROSTHESIS

(71) Applicant: B&D Dental Corp., West Valley City, UT (US)

(72) Inventors: Daniel Yonil Jung, Sandy, UT (US); Yunoh Jung, Sandy, UT (US)

(73) Assignee: B & D Dental Corp., West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,601

(22) Filed: May 30, 2014

(65) Prior Publication Data

US 2015/0111172 A1 Apr. 23, 2015

Related U.S. Application Data

(60) Provisional application No. 61/892,345, filed on Oct. 17, 2013, provisional application No. 61/909,812, filed on Nov. 27, 2013.

(51) Int. Cl.
*A61C 13/00* (2006.01)
*A61C 5/10* (2006.01)
(Continued)

(52) U.S. Cl.
CPC ............... *A61C 13/0003* (2013.01); *A61C 5/10* (2013.01); *A61C 13/0004* (2013.01);
(Continued)

(58) Field of Classification Search
CPC ............. A61C 13/0003; A61C 13/225; A61C 5/08–5/10; A61C 13/0004; A61C 13/26; A61C 13/09; A61C 19/063; A61C 9/002

USPC ........... 433/218–220, 222.1–223, 202.1, 204, 433/172–176, 201.1
See application file for complete search history.

(56) References Cited

U.S. PATENT DOCUMENTS 2,770,040 A 11/1956 Moyer
2,891,313 A 6/1959 Crowley
(Continued)

FOREIGN PATENT DOCUMENTS

CN 101703451 B 5/2010
EP 0380796 8/1990
(Continued)

OTHER PUBLICATIONS

PCT Application PCT/US14/40554; filed Jun. 2, 2014; B&D Dental Corp.; International Search Report mailed Oct. 31, 2014.

*Primary Examiner* — Edward Moran
(74) *Attorney, Agent, or Firm* — Thorpe North & Western, LLP

(57) ABSTRACT

A method of making a dental crown or bridge restoration includes forming a precursor crown outside of a patient's mouth with a first restorative material, with a buccal contour on the buccal wall substantially the same as a buccal contour on a final crown restoration, and an open space on or around at least one of the mesial side wall or the distal side wall; and filling and securing a second material, different from the first restorative material, inside the open space or pocket of the precursor crown while outside the patient's mouth, and with the precursor crown having a strength substantially equivalent to the final crown restoration, and with the buccal contour being substantially the same as the buccal contour on the final crown, prior to filling and securing the second material.

33 Claims, 23 Drawing Sheets

(51) Int. Cl.
- *A61C 13/225* (2006.01)
- *A61C 13/271* (2006.01)
- *A61C 19/06* (2006.01)
- *A61C 9/00* (2006.01)
- *A61C 13/09* (2006.01)

(52) U.S. Cl.
CPC .............. *A61C 13/225* (2013.01); *A61C 13/26* (2013.01); *A61C 19/063* (2013.01); *A61C 9/002* (2013.01); *A61C 13/09* (2013.01)

(56) References Cited

U.S. PATENT DOCUMENTS

| | | | |
|---|---|---|---|
| 3,423,829 A | 1/1969 | Halpern et al. | |
| 3,468,028 A | 9/1969 | Sunter | |
| 3,481,772 A | 12/1969 | MaoNairn et al. | |
| 3,647,488 A | 3/1972 | Brigham et al. | |
| 4,231,740 A | 11/1980 | Shoher et al. | |
| 4,299,574 A | 11/1981 | Neihart | |
| 4,515,910 A | 5/1985 | Rawls et al. | |
| 4,572,920 A | 2/1986 | Rawls et al. | |
| 4,585,417 A * | 4/1986 | Sozio et al. | 433/202.1 |
| 4,600,389 A | 7/1986 | Schwartz | |
| 4,612,053 A | 9/1986 | Brown et al. | |
| 4,654,007 A | 3/1987 | Sigler et al. | |
| 4,678,435 A * | 7/1987 | Long | 433/218 |
| 4,722,689 A | 2/1988 | Corbett | |
| 4,732,617 A | 3/1988 | Causton et al. | |
| 4,772,325 A * | 9/1988 | Kwan et al. | 106/35 |
| 4,775,646 A | 10/1988 | Hench et al. | |
| 4,871,786 A | 10/1989 | Aasen et al. | |
| 4,877,402 A | 10/1989 | Hirabayashi et al. | |
| 5,074,916 A | 12/1991 | Hench et al. | |
| 5,145,520 A | 9/1992 | Kokubo et al. | |
| 5,304,586 A | 4/1994 | Hammesfahr et al. | |
| 5,306,338 A | 4/1994 | Tsunekawa | |
| 5,330,353 A | 7/1994 | Wavrin | |
| 5,336,264 A | 8/1994 | Constanz et al. | |
| 5,496,399 A | 3/1996 | Ison et al. | |
| 5,508,342 A * | 4/1996 | Antonucci et al. | 524/788 |
| 5,527,836 A | 6/1996 | Yamamuro et al. | |
| 5,545,254 A | 8/1996 | Chow et al. | |
| 5,639,239 A | 6/1997 | Earle | |
| 5,652,016 A | 7/1997 | Imura et al. | |
| 5,695,339 A | 12/1997 | Abere | |
| 5,718,924 A | 2/1998 | Braden et al. | |
| 5,735,942 A | 4/1998 | Litkowski et al. | |
| 5,738,113 A | 4/1998 | Connelly | |
| 5,782,971 A | 7/1998 | Constantz et al. | |
| 5,824,720 A | 10/1998 | Nowak et al. | |
| 5,876,208 A | 3/1999 | Mitra et al. | |
| 5,883,153 A | 3/1999 | Roberts et al. | |
| 5,891,233 A | 4/1999 | Salonen et al. | |
| 5,908,879 A | 6/1999 | Kawashima et al. | |
| 5,927,984 A * | 7/1999 | Lin | 433/218 |
| 6,077,989 A | 6/2000 | Kandel et al. | |
| 6,086,374 A | 7/2000 | Litkowski et al. | |
| 6,325,992 B1 | 12/2001 | Chow et al. | |
| 6,334,775 B2 | 1/2002 | Xu et al. | |
| 6,386,865 B1 | 5/2002 | Suh et al. | |
| 6,455,609 B1 | 9/2002 | Rueggeberg et al. | |
| 6,793,725 B2 | 9/2004 | Chow et al. | |
| 6,835,066 B2 * | 12/2004 | Iiyama et al. | 433/223 |
| 6,860,737 B2 | 3/2005 | Ulso | |
| 6,949,251 B2 | 9/2005 | Dalal et al. | |
| 7,018,460 B2 | 3/2006 | Xu et al. | |
| 7,090,720 B2 | 8/2006 | Kessler et al. | |
| 7,255,562 B2 | 8/2007 | Rusin et al. | |
| 7,323,160 B2 | 1/2008 | Algar et al. | |
| 7,416,602 B2 | 8/2008 | Murphy et al. | |
| 7,491,694 B2 | 2/2009 | Reynolds et al. | |
| 7,709,029 B2 | 5/2010 | Chow et al. | |
| 7,726,970 B2 * | 6/2010 | Worthington | 433/218 |
| 7,845,947 B2 | 12/2010 | Rusin et al. | |
| 7,892,346 B2 | 2/2011 | Insley et al. | |
| 8,217,173 B2 | 7/2012 | Xu et al. | |
| 8,512,741 B2 | 8/2013 | Tan et al. | |
| 8,609,071 B2 | 12/2013 | Reynolds | |
| 8,636,928 B2 | 1/2014 | Sun et al. | |
| 2002/0137812 A1 | 9/2002 | Chow et al. | |
| 2003/0167093 A1 | 9/2003 | Xu et al. | |
| 2004/0065228 A1 | 4/2004 | Kessler et al. | |
| 2004/0158194 A1 | 8/2004 | Wolff et al. | |
| 2004/0224284 A1 * | 11/2004 | Saito et al. | 433/202.1 |
| 2005/0020720 A1 | 1/2005 | Dickens et al. | |
| 2005/0048113 A1 | 3/2005 | Abdulrazik | |
| 2007/0221093 A1 | 9/2007 | Erdrich et al. | |
| 2008/0305053 A1 | 12/2008 | Lee et al. | |
| 2009/0317772 A1 | 12/2009 | Rusin | |
| 2010/0086895 A1 | 4/2010 | Randall | |
| 2010/0272764 A1 | 10/2010 | Latta et al. | |
| 2012/0100505 A1 * | 4/2012 | Huynh | 433/201.1 |
| 2012/0115106 A1 | 5/2012 | Qian et al. | |
| 2013/0130203 A1 | 5/2013 | Velamakanni et al. | |
| 2013/0171220 A1 | 7/2013 | Hill et al. | |

FOREIGN PATENT DOCUMENTS

| | | |
|---|---|---|
| EP | 0509516 | 10/1992 |
| EP | 0873107 | 10/1998 |
| JP | 4601027 B2 | 6/2002 |
| WO | WO 94/23944 | 10/1994 |
| WO | WO 97/18792 | 5/1997 |
| WO | WO 00/69393 | 11/2000 |
| WO | WO 2007/001624 A | 1/2007 |
| WO | WO/2007/144662 | 12/2007 |
| WO | WO/2008/086566 | 7/2008 |
| WO | WO2012/101432 | 8/2012 |

* cited by examiner top view bottom view mesial side view

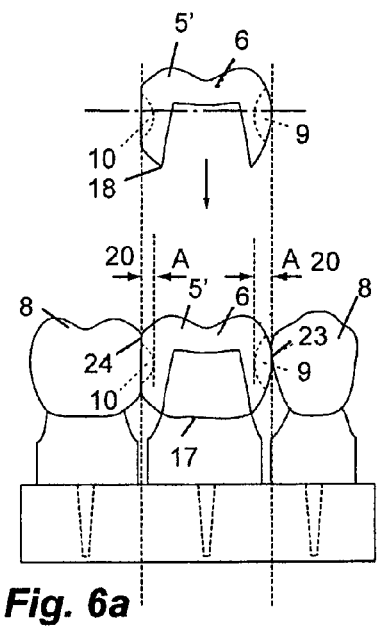
Fig. 6a
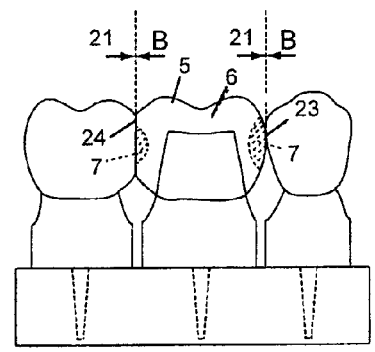
Fig. 7a
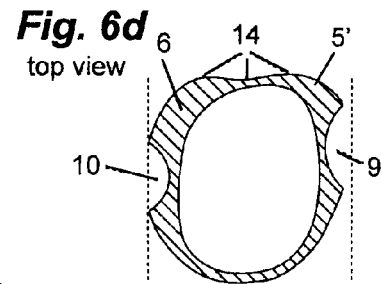
Fig. 6d top view
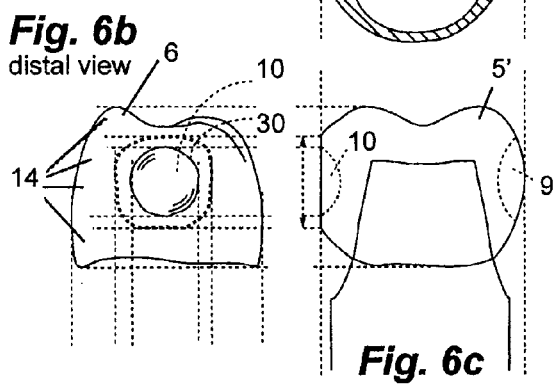
Fig. 6b distal view
Fig. 6c buccal view
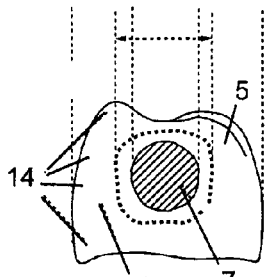
Fig. 7b
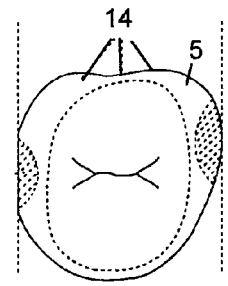
Fig. 7c occlusal view
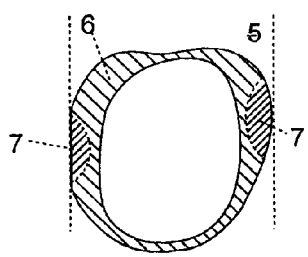
Fig. 7d

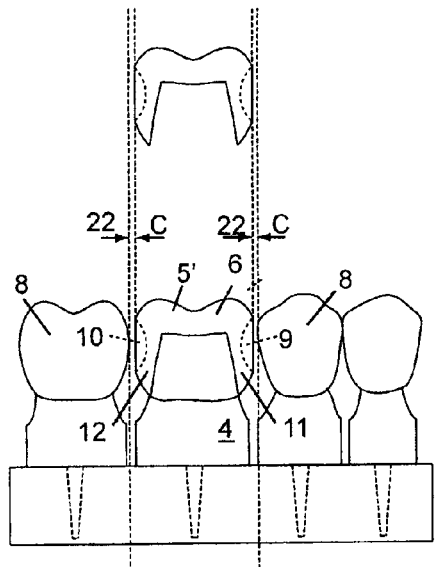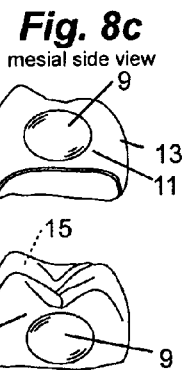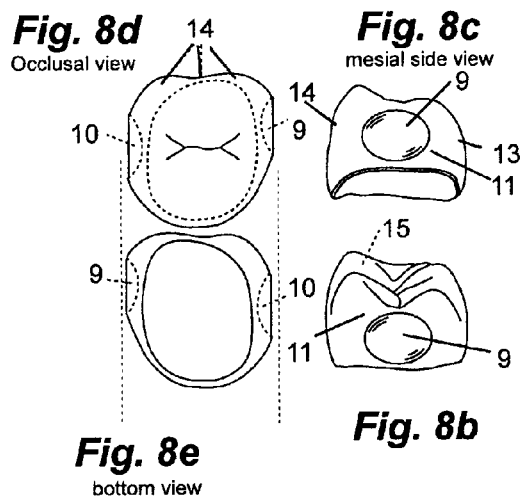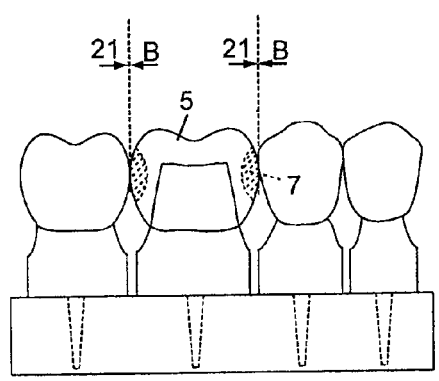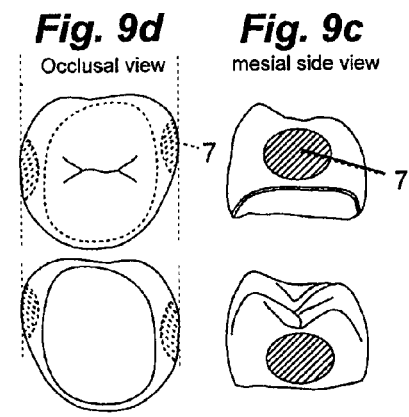
Fig. 8a Buccal view
Fig. 8d Occlusal view
Fig. 8c mesial side view
Fig. 8b
Fig. 8e bottom view
Fig. 9a Buccal view
Fig. 9d Occlusal view
Fig. 9c mesial side view
Fig. 9b
Fig. 9e bottom view

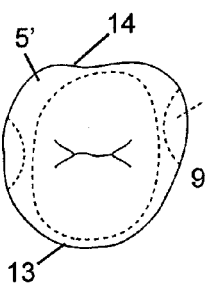
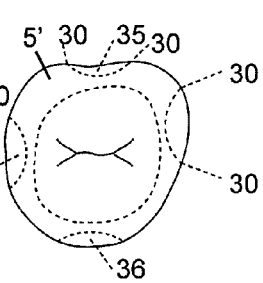
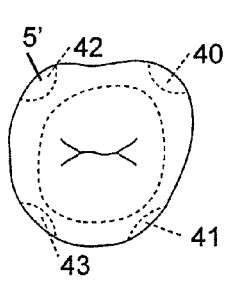
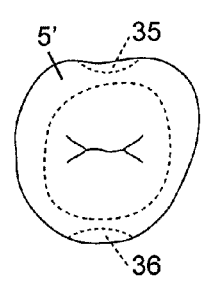
Fig. 10a    Fig. 10e    Fig. 11a    Fig. 12a
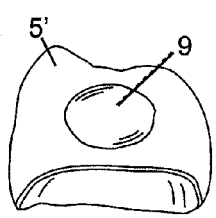
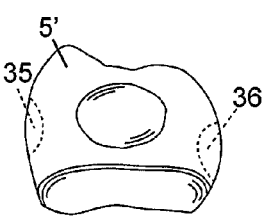
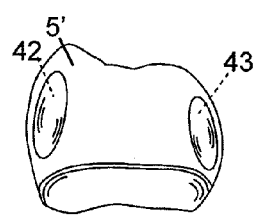
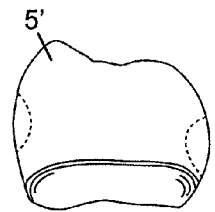
Fig. 10b    Fig. 10f    Fig. 11b    Fig. 12b
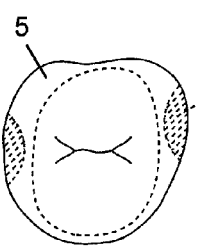
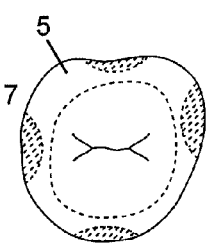
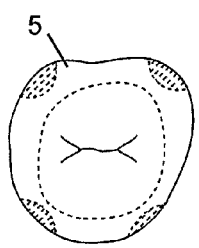
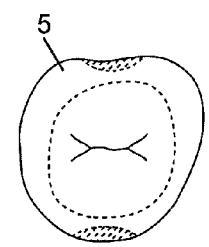
Fig. 10c    Fig. 10g    Fig. 11c    Fig. 12c
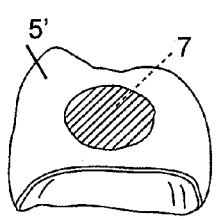
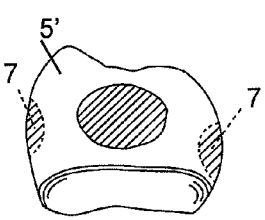
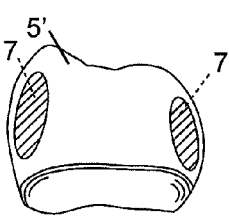
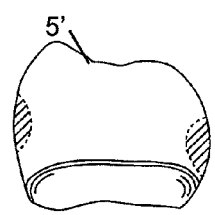
Fig. 10d    Fig. 10h    Fig. 11d    Fig. 12d Buccal View Mesial View Bottom View Mesial View mesial side view mesial side view Fig. 19a buccal view Fig. 19b buccal view Fig. 19c occlusal view Fig. 19d mesial view Occlusal View Occlusal View Occlusal View Occlusal View Buccal view

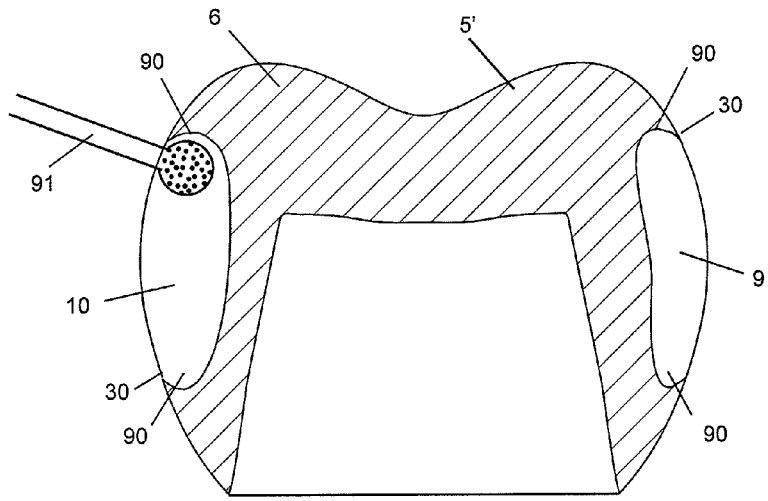
Fig. 26
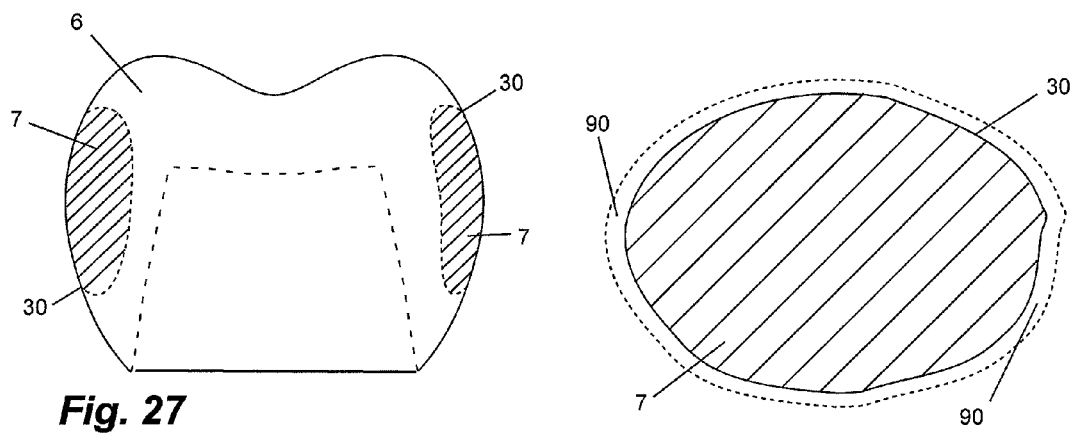
Fig. 27
Fig. 30
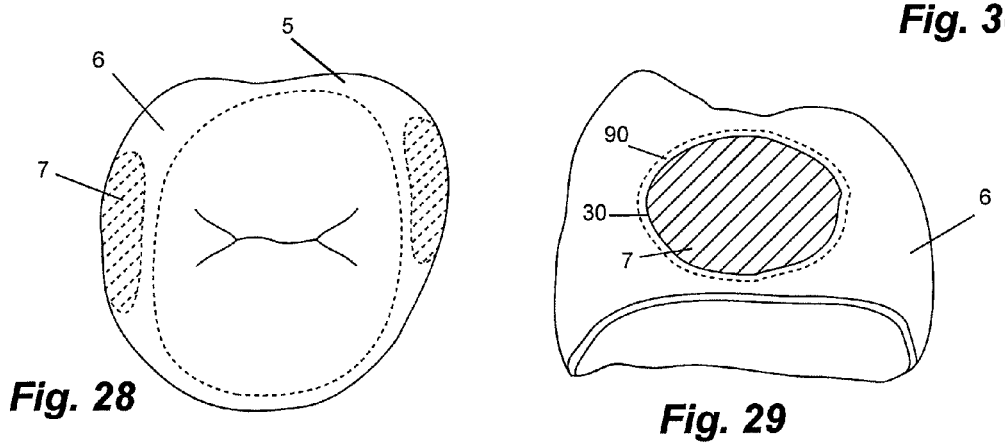
Fig. 28
Fig. 29 buccal view occlusal view mesial view

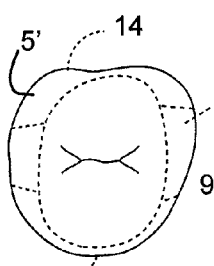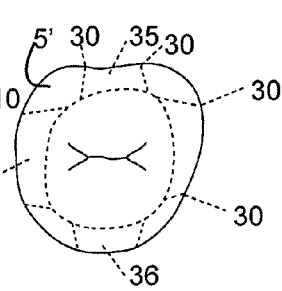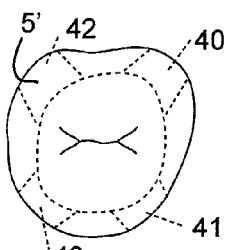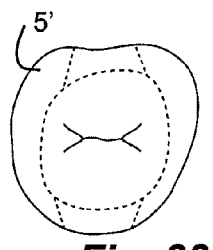
*Fig. 31a*  *Fig. 31e*  *Fig. 32a*  *Fig. 33a*
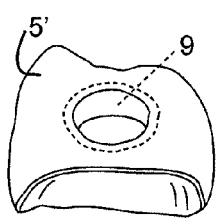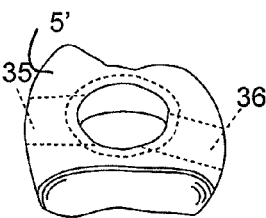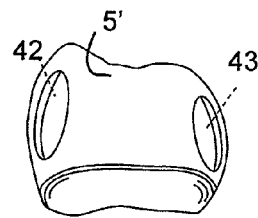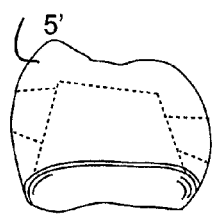
*Fig. 31b*  *Fig. 31f*  *Fig. 32b*  *Fig. 33b*
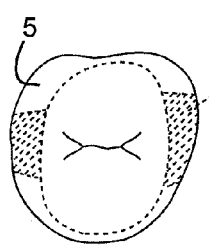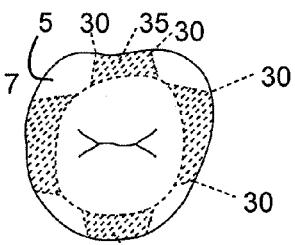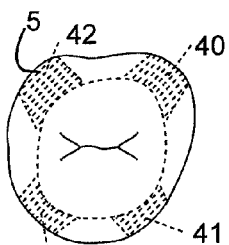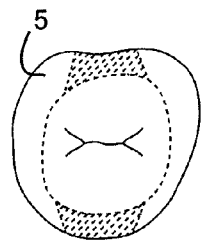
*Fig. 31c*  *Fig. 31g*  *Fig. 32c*  *Fig. 33c*
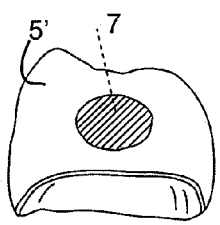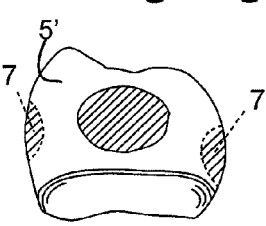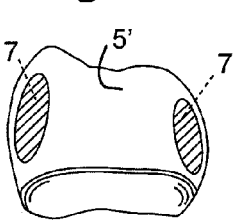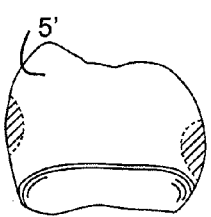
*Fig. 31d*  *Fig. 31h*  *Fig. 32d*  *Fig. 33d*

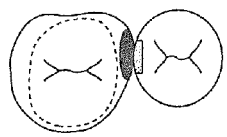
Fig. 36a
Phase 1
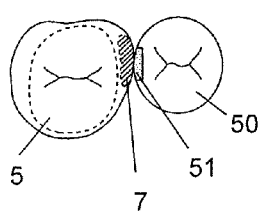
Fig. 36b
Phase 2
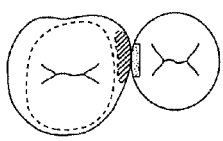
Fig. 36c
Phase 3
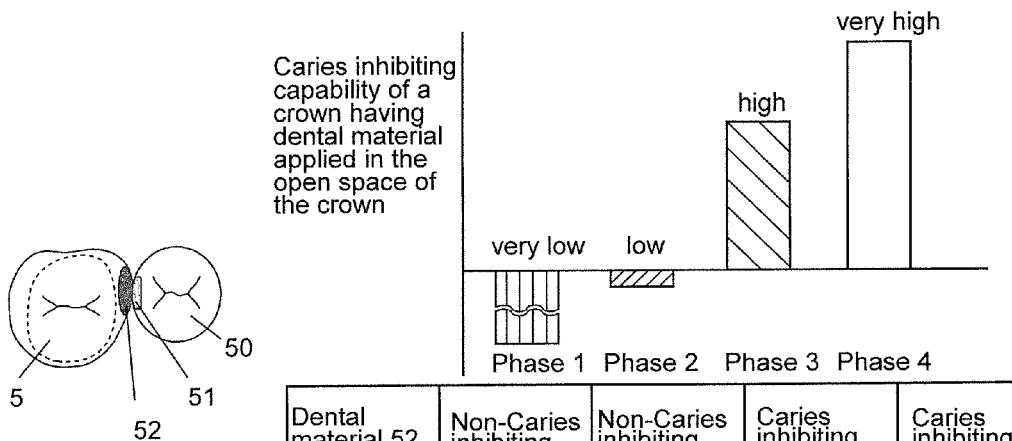
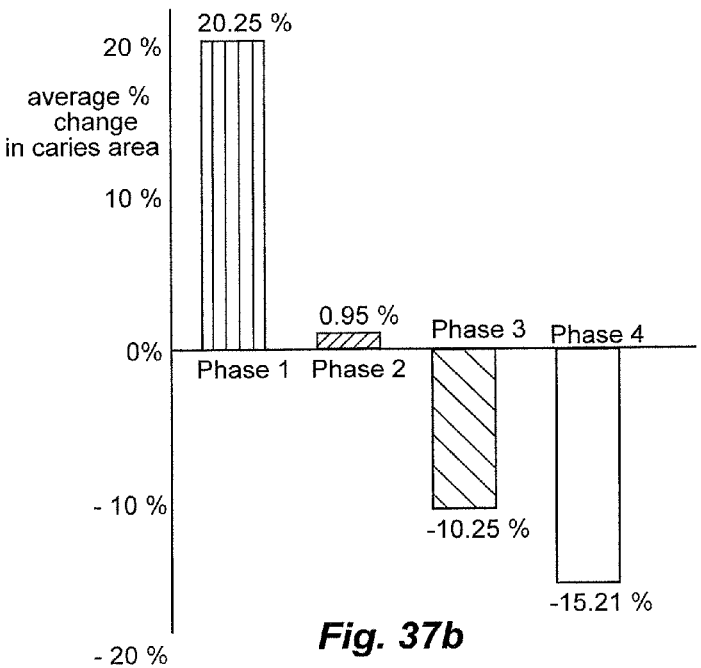
Fig. 36d
Phase 4

Forming, with a primary material, indirect crown or bridge dental restoration having occlusal, mesial, buccal, distal, and lingual wall, with buccal wall facing the cheek side, and lingual wall facing the tongue side, and mesial wall facing the distal side of the adjacent tooth, and distal wall facing mesial side of the adjacent tooth, and with all walls connected to form a concavity therein, and the concavity facing a prepared tooth cut by a dentist or implant abutment and the restoration having an open contact portion of the outside of at least one of the mesial and distal walls of the primary material of the indirect crown or bridge dental restoration to create an open space therein and leave at least a part of the contact area open and then,

↓ applying a secondary material of dental caries inhibition on the outside of the at least one of the mesial and distal wall of the indirect crown or bridge dental restoration in a way to deposit a mass of secondary material in the open contact area and then,

↓ hardening the secondary material so that it doesn't separate from the primary material and then,

↓ close the contact by processing the indirect crown or bridge dental restoration so that the outside of the at least one of the mesial and distal contact of the restoration can directly contact at least one of the adjacent tooth

*Fig. 39* making the inorganic precursor crown outside of a mouth, with a first material, with an open space on or around at least one of the mesial and distal areas, said open space perimeter existing either inside the contact area perimeter, or completely encompassing the contact area perimeter, or partially inside and partially outside the contact area perimeter, or completely outside the contact area perimeter; followed by

applying a fluoride-releasing second material different from the first material comprising polymers and fillers inside the said open space of the precursor crown outside the mouth,such that the crown is made not to have more than 20 milligram of daily released fluoride ion(F) as measured according to ISO 10359 measuring method; followed by

curing the fluoride-releasing material outside the mouth in such a way as not to get separated from the first material, and the flexural strength of the first material is greater than or equal to the fluoride releasing material as measured according to ISO 6872; and then followed by

seating the fluoridated crown on the patients prepared tooth in a fixed way

*Fig. 40*

METHOD OF MAKING A DENTAL PROSTHESIS

PRIORITY CLAIM

Priority is claimed to U.S. Provisional Patent Application Ser. Nos. 61/892,345, filed Oct. 17, 2013, and 61/909,812, filed Nov. 27, 2013, which are hereby incorporated herein by reference in their entirety.

BACKGROUND

1. Field of the Invention

The present invention relates generally to a method for making a dental restoration or prosthesis, such as a crown or a bridge. In particular, the present invention relates to a method for making a dental restoration with a second material filling a pocket in the dental restoration.

2. Related Art

Minimal intervention is a key phrase in today's dental practice. Minimal intervention dentistry (MID) focuses on the least invasive treatment options possible in order to minimize tissue loss and patient discomfort. Concentrating mainly on prevention and early intervention of caries, MID's first basic principle is the remineralization of early carious lesions, advocating a biological or therapeutic approach rather than the traditional surgical approach for early surface lesions. One of the key elements of a biological approach is the usage and application of caries inhibiting (or remineralizing) agents to tooth structure (enamel and dentin lesions). These agents are part of a new era of dentistry aimed at controlling the demineralization/remineralization cycle, depending upon the microenvironment around the tooth.

Dental caries is a multifactorial disease caused by the interaction of dietary sugars, dental biofilm and the host's dental tissue within the oral environment (Buzalaf M A R, Fluoride and the Oral Environment, Monogr Oral Sci, Basel, Karger, 2011, vol 22, p 97-114). It is the cumulative result of consecutive cycles of demineralization and remineralization at the interface between the biofilm and the tooth surface. Oral bacteria excrete acid after consuming sugar, leading to demineralization (Fejerskow O, Kidd, E A, Nyvad B, Baclum V, Defining the disease: an introduction: in Fejerskov O, Kidd E (eds): Dental Caries—The Disease and its Clinical Magement, ed 2, Oxford, Blackwell Munksgaard, 2008, p 3-6). Upon this acid challenge, the hydroxyapatite crystals are dissolved from the subsurface. Remineralization is the natural repair process for non-cavitated lesions. It relies on calcium and phosphate ions, assisted by fluoride, to rebuild a new surface on the existing crystal remnants in the subsurface. The remineralized crystals are less acid soluble than the original ones (Featherstone J D, Dental Caries: a dynamic disease process, Aust Dent J, 2008; 53(3):286-91).

When the enamel and dentin no longer have adequate structure to maintain their mineral framework, cavitation takes place and remineralization is an insufficient treatment. Tooth preparation and restoration are now required. Although most restorative materials are inert with respect to the biological tissues of the tooth, some are bioactive. Bioactive restorative materials actually interact with or affect the biological tissues. They effectively work with the dental hard tissues to harden and "heal" them. The most widely used bioactive (caries inhibiting) restorative materials are calcium, phosphate, and fluoride. These agents release calcium ions, phosphate ions, and fluoride ions, respectively. Silver, copper, and zinc can also be used to inhibit the caries causing microbes.

It is well established that topically applied fluoride ions as a typical example of CIMs (caries inhibition materials), through integration into the mineral component of enamel and dentin, can function to reduce the incidence and progression of dental caries. (J. M. Ten Cate, "Current concepts on the theories of the mechanism of action of fluoride," ActaOdontologicaScandinavica, vol. 57, no. 6, pp. 325-329, 1999.) (C. González-Cabezas, "The chemistry of caries: remineralization and demineralization events with direct clinical relevance," Dental Clinics of North America, vol. 54, no. 3, pp. 469-478, 2010). Fluoride complexes have the ability to promote dental tissue remineralization in addition to increasing the resistance of tooth structure to demineralization. (W. Evans, "Conference report: a joint IADR/ORCA international symposium—fluorides: mechanisms of action and recommendations for use," Journal of Dental Research, vol. 68, no. 7, pp. 1215-1216, 1989). Fluoride can be made available to tooth surfaces through several methods, including via dentifrices, mouth rinses, and fluoridated water intake. It can also be used as a FRRM (Fluoride releasing restorative material) generally in the form of glass ionomer restorative material/cements or RMGI (resin-modified glass ionomer) restorative material/cements.

Some fluoride releasing dental materials are known. Some are fluoride ion releasing materials, mostly in a resin matrix. Often, the material is applied on the natural tooth directly inside a patients mouth. Some of these materials are an adhesive cement to seat a crown. For example, see: U.S. Pat. No. 4,515,910 (Raws et al); U.S. Pat. No. 4,572,920 (Zimmerman et at); U.S. Pat. No. 4,732,617 (Causton et al), U.S. Pat. No. 4,775,646 (Hench et al); U.S. Pat. No. 4,871,786 (Aasen et al); EP application 0,380,796 (Danielson); U.S. Pat. No. 5,304,586 (Hammesfahr et al); EP Application 0,509,516; U.S. Pat. No. 5,306,338 (Tsunekawa); International publication number WO 94/23944 (Sladek); U.S. Pat. No. 5,824,720 (Nowak et al); EP application 0,772,709 (Braden); EP application 0,873,107 (Mitra et al); U.S. Pat. No. 5,718,924 (Braden et al); U.S. Pat. No. 5,883,153 (Roberts et al); U.S. Pat. No. 5,908,879 (Kawashima et al); U.S. Pat. No. 5,738,113 (Connelly); U.S. Pat. No. 6,334,775 (Xu et al); International publication number WO00/69393 (Brennan et al); U.S. Pat. No. 7,255,562 (Rusin et al); U.S. Pat. No. 7,491,694 (Reynolds et al); U.S. Pat. publication 2008/0305053 (Lee et al); U.S. Pat. No. 8,217,173 (Xu et al); and International publication number 2012/101432.

Also, some calcium and phosphate releasing dental material are known. Some are calcium ion and/or phosphate ion releasing materials, mostly in a resin matrix. Some of the materials are applied on the natural tooth directly inside a patient's mouth. Some of these materials can be used as an adhesive cement to seat a crown. For example, see: U.S. Pat. No. 7,491,694 (Reynolds et al); U.S. Pat. No. 5,782,971 (Constanz et al); U.S. Pat. No. 7,892,346 (Insley et al); U.S. Pat. No. 8,609,071 (Reynolds); U.S. Pat. No. 7,416,602 (Murphy et al); U.S. Pat. No. 8,512,741 (Tan et al); U.S. Pat. No. 7,709,029 (Chow et al); U.S. Pat. No. 7,018,460 (Xu et al); U.S. Pat. No. 6,949,251 (Dalai et al); 2005040286 (Rusin et al); 20050020720 (Dickens et al); U.S. Pat. No. 6,793,725 (Chow et al); 20030167093 (Xu et al); 20020137812 (Chow et al); U.S. Pat. No. 6,325,992 (Chow et al); U.S. Pat. No. 6,077,989 (Kandel et al); U.S. Pat. No. 5,782,971 (Constanz et al); U.S. Pat. No. 5,652,016 (Imura et al); U.S. Pat. No. 5,545,254 (Chow et al); U.S. Pat. No. 5,508,342 (Antonucci et al); U.S. Pat. No. 5,496,399 (Ison et al); U.S. Pat. No. 5,336,264 (Constanz et al); U.S. Pat. No. 4,612,053 (Brown et al).

Also, some bioactive dental materials are known. Some bioactive dental materials are applied on a natural tooth directly inside a patient's mouth. Some of these materials can be used as an adhesive cement to seat a crown. For example, see: U.S. Pat. No. 6,709,644 (Day et al); U.S. Pat. No. 7,090,720 (Kessler et al); WO/2007/144662 (Hill et al); U.S. Pat. No. 7,329,129 (Cook et al); US20040065228 (Kessler et al); US20070221093 (Erdrich et al); U.S. Pat. No. 6,086,374 (Litkowski et al); U.S. Pat. No. 5,891,233 (Salonen et al); U.S. Pat. No. 5,735,942 (Likowski et al); U.S. Pat. No. 5,527,836 (Yamamuro et al); U.S. Pat. No. 5,074,916 (Hench et al); U.S. Pat. No. 5,145,520 (Kokubo et al); U.S. Pat. No. 5,527,836 (Yamamuro et al); US 20130171220 (Hill et al); WO/1202/002996 (Bringley et al).

A bioactive delivery device for delivering a bioactive solution to the maxillary or mandibular, periodontal and/or mucosal tissues is known. For example, see WO/2008/086566 (Cochrane et al).

Methods of making dental crowns are known. Some include an artificial tooth which comprises an outer shell of esthetic porcelain and an inner core selected from reinforcing strong porcelain, synthetic resin, and a combination of synthetic resin and reinforcing strong porcelain. For example, see U.S. Pat. No. 3,423,829 (Halpern et al).

A dental prosthesis structure is known including a metal base contoured in a desired form and having a glass veneer of substantially the same coefficient of expansion as the metal base bonded to the metal base. For example, see U.S. Pat. No. 3,481,772 (MaoNairn et al).

A preformed artificial crown for restoring a damaged tooth is known. For example, see U.S. Pat. No. 3,468,028 (Sunter).

A composition and method of preparing a model base in the manufacture of dental prosthesis is known in which the model base is made of alkali phosphate and alkaline-earth fluoride. For example, see U.S. Pat. No. 3,647,488 (Kristin et al).

A porcelain superstructure surrounding a metal substructure composed of a framework of relatively thin metal members interconnected to form concavities within the porcelain superstructure is known. U.S. Pat. No. 4,231,740 (Shoher et al)

See also U.S. Pat. No. 4,299,574 (Neihart); U.S. Pat. No. 4,600,389 (Schwartz); U.S. Pat. No. 4,654,007 (Sigler et al); U.S. Pat. No. 4,722,689 (Corbetta); U.S. Pat. No. 4,877,402 (Hirabayashi et al); U.S. Pat. No. 5,695,339 (Abera); U.S. Pat. No. 6,386,865 (Suh et al).

There is no agreement in the literature in regards to the question of what quantity of fluoride has to be released from a filling material in order for it to provide a reliable caries-inhibiting action (R. W. Phillips, "Restorative Materials Containing fluoride, Journal of American Dental Association 116 (1988) 762-763). In view of clinical findings with various fluoride-releasing filling materials, it is, however, to be noted that the quantity of fluoride which is released by glass ionomer cements can reduce the formation of secondary caries to an extent that is clinically relevant (G. Wesenberg et al., J. Oral Rehabil. 7 (1980) 175-184). Also, it has been shown that in the case of so-called composite filling materials that display no or very little fluoride release, there is a particular susceptibility to attack from secondary caries (E. A. M. Kidd, Br. Dent. J. 144 (1978) 139-142).

Fluoride (F—) release is a desirable attribute for a material used in some dental applications. In general, materials that release greater amounts of fluoride have greater caries prevention potential and are desirable. For direct treatment methods to be directly used inside the patient's mouth, there are many dental materials being used that release fluoride including silicate cements, glass ionomer cements, glass ionomer hybrid (resin-modified) cements, and fluoride releasing composite resins. These materials are used either for filling materials after removal of caries or for adhesive material between the crown and prepared tooth. Also, it has been well known that fluoride releasing materials, as one example of a caries inhibiting material, release fluoride ions and recharges the ions when the fluoride ion level is high inside the mouth from the fluoridated dentifrices over long period of time.

SUMMARY OF THE INVENTION

It has been recognized by the present inventors that it would be advantageous to develop a dental prosthesis, such as dental crown or bridge restoration, and method for making the dental prosthesis with a second material filling an open space or pocket in a precursor prosthesis of a first restorative material.

The invention presents a method of making a dental crown or bridge restoration having occlusal, mesial side, buccal, distal side, and lingual walls. The buccal wall is to be adjacent a patient's cheek; the lingual wall is to be adjacent a patient's tongue; the occlusal wall is to face an opposing tooth; and the mesial and the distal side walls are each to face a different adjacent tooth. The walls are connected to define a concavity therein configured to receive and match a prepared tooth, or an implant abutment. The method comprises, in sequence, first receiving a margin line information of the prepared tooth or the implant abutment. Next, a precursor crown or bridge restoration is formed outside of a patient's mouth with a first restorative material. Forming the precursor restoration comprises: creating a restoration margin line corresponding with the margin line information of the prepared tooth or the implant abutment; creating a buccal contour on the buccal wall of the precursor crown substantially the same as or proportion to a desired final buccal contour on a final crown or bridge restoration; and creating an open space with an open space perimeter on or around at least one of the mesial side wall or the distal side wall. Next, a second material, different from the first restorative material, is filled and secured inside the open space of the precursor crown or bridge restoration while outside the patient's mouth, and with the precursor crown or bridge restoration having a strength substantially equivalent to the final crown or bridge restoration, and with the buccal contour on the buccal wall being substantially the same as the buccal contour on the final crown or bridge restoration, prior to filling and securing the second material.

In addition, the invention provides a method for making a dental restoration to receive and match a prepared tooth or an implant abutment. The method comprises forming a precursor restoration from a first restorative material. The dental restoration has occlusal, mesial side, buccal, distal side, and lingual walls. The buccal wall is to be adjacent a patient's cheek; the lingual wall is to be adjacent a patient's tongue; the occlusal wall is to face an opposing tooth; and the mesial and the distal side walls each face a different adjacent tooth. A concavity is formed opposite the occlusal wall and between the walls to receive and match the prepared tooth or the implant abutment. The buccal wall is contoured to have substantially a desired final contour. At least one open space is formed in an exterior of at least one of the mesial side wall or the distal side wall. The precursor restoration is heat hardened, defining a hardened precursor restoration. A second material, different than the first material, is disposed and secured in the at least one open space of the hardened precursor restoration after final heat hardening. The second material has an exposed exterior surface.

In addition, the invention provides a method for making a dental restoration to receive and match a prepared tooth or an implant abutment. The method comprises receiving a margin line information of the prepared tooth or the implant abutment. A precursor restoration is formed from a first restorative material outside of a patient's mouth. The precursor restoration has occlusal, mesial side, buccal, distal side, and lingual walls; with the buccal wall to be adjacent a patient's cheek, the lingual wall to be adjacent a patient's tongue, the occlusal wall to face an opposing tooth, and the mesial and the distal side walls each to face a different adjacent tooth. A restoration margin line is created corresponding with the margin line information of the prepared tooth or the implant abutment. A concavity is opposite the occlusal wall and between the walls to receive and match the prepared tooth or the implant abutment. The buccal wall is contoured to have substantially a desired final contour. At least one open space is formed in an exterior of at least one of the mesial side wall or the distal side wall, that would have an open contact relationship, after final heat hardening, with respect to the corresponding adjacent tooth due to the at least one open space. The precursor restoration is heat hardened, defining a hardened precursor restoration. A second material, different than the first material, is disposed and secured in the at least one open space of the hardened precursor restoration after heat hardening and while outside the patient's mouth, defining a final restoration. The second material has an exposed exterior surface. The first material has a higher temperature tolerance than the second material. The final restoration is seated and secured on the prepared tooth or the implant abutment inside the patient's mouth. The second material has a closed contact relationship with the corresponding adjacent tooth.

Furthermore, the invention provides a method for making a dental restoration to receive and match a prepared tooth or an implant abutment. The method comprises forming a precursor restoration from a first restorative material to have occlusal, mesial side, buccal, distal side, and lingual walls; with the buccal wall to be adjacent a patient's cheek, the lingual wall to be adjacent a patient's tongue, the occlusal wall to face an opposing tooth, and the mesial and the distal side walls each to face a different adjacent tooth. A concavity is formed opposite the occlusal wall and between the walls to receive and match the prepared tooth or the implant abutment. The buccal wall is contoured to have substantially a desired final contour. At least one open space is formed in an exterior of at least one of the mesial side wall or the distal side wall. The precursor restoration is heat hardened when the first material does not have a strength substantially equivalent to a final restoration. A second material, different than the first material, is disposed and secured in the at least one open space of the precursor restoration with the precursor restoration having a desired contour on the buccal wall substantially the same as that of the final restoration.

In addition, it has been recognized by the present inventors that there is a need for a dental prosthesis, such as a crown or bridge, to 1) release caries inhibiting bioactive agents for an extended period of time from a mass or bulk that sustains a continual release of ions, instead of a short period of time, directly towards the unrestored adjacent tooth, and 2) have a high flexural strength that comes ultimately from the first material in a stress-bearing area over at least 100 Mpa, preferably over 150 Mpa as in the first material being a glass polymer crown, preferably over 200 Mpa as in the first material being a nano ceramic crown, preferably over 400 Mpa as in the first material being a glass ceramic crown, preferably over 1,000 Mpa as in the first material being a zirconia crown, and 3) can withstand high temperature, preferably over 300° C., heat treatment in post processing for strengthening purposes.

The present invention provides a method for making a dental prosthesis or restoration, such as a dental crown or bridge, that is capable of inhibiting caries so that the adjacent natural teeth can get the benefit of reduced caries incidents. More specifically, the present invention presents a method of making a dental crown having a caries inhibiting material applied to the open space created on or around at least one of the mesial and distal contact areas so that the natural teeth contacting the crown can achieve a reduced occurrence of dental caries.

The present invention provides a method of making a dental crown capable of caries inhibition. A second material, such as a caries inhibition material, can be applied inside the pocket or open space created on or round at least one of the mesial and/or distal sides of a first material of the dental crown in a substantial mass or bulk form to work as a reservoir to retain the efficacy of the continued release of ions of bioactive materials. The present inventors have realized the following problems:

Problem I: CIMs or FRRMs Currently have Limited Use Only as Direct Treatment Methods by Dentists FRRMs (fluoride releasing restorative material) as typical examples of CIMs (caries inhibition materials) have been known in dentistry for almost over thirty years. But FRRMs so far have been used only in a limited fashion by dentists as 1) an adhesive cement material to seat the permanent indirect restoration inside the patient's mouth, and 2) a filling composite replacing carious natural tooth directly inside the patient's mouth. Direct treatment method means that the treatment or restoration is made directly inside the patient's mouth, not involving the separate crown making process, for example, by a dental technician.

Problem II: CIMs or FRRMs Currently are not Used in Making Permanent Crowns

A dental crown is a restoration made outside of a patient's mouth to replace the removed portion (enamel and dentin) of the ground natural tooth. Teeth are ground down by dentists for various reasons, for example, to remove the carious area or for root canal treatment. Dental crowns and bridges are the typical type of indirect treatment that is done outside of a patient's mouth. Benefits of the indirect method as opposed to the direct method are that the restorations are 1) much stronger due to the high temperature heat treatment that the restorations (crowns and bridges) undergo, and 2) aesthetically superior since dental technicians take more time to create better looking restorations. The only application of involving FRRMs or CIMs (caries inhibition materials) for use with crowns is to use it to seat the crown restoration onto the ground tooth. The main reasons for this are that current FRRMs or caries inhibition materials 1) have an undesirably and/or unacceptably lower strength by nature, and 2) is not compatible with high-temperature post processing that most of the crowns require.

Problem III: CIMs (Caries Inhibition Materials), and FRRMs have a Low Strength and Cannot be Used for High Temperature Heat Treatment CIMs and FRRMs cannot be used alone to make a crown due to the weak nature of the material. The main limitation of the glass ionomer cements as one form of FRRM is their relative lack of strength and low resistance to abrasion and wear. Conventional low-viscosity glass ionomer cements have low flexural strength (with flexural strength usually lower than 80 Mpa) but high modulus of elasticity, and are therefore very brittle and prone to bulk fracture. Some glass cements are arguably stronger than conventional materials but their fracture resistance remains low. The resin-modified glass-ionomer (RMGI) materials as another form of FRRM have been shown to have significantly higher flexural and tensile strengths and lower modulus of elasticity than the conventional materials. They are therefore more fracture-resistant but their wear resistance is not adequate. In addition, their strength properties are still far inferior (around 100 Mpa) to those of composite-resins, and so should not be subject to undue occlusal load unless they are well supported by surrounding tooth structure. For example, the observed mechanical property degradation of one of the leading brand RMGIs in both neutral and acidic conditions can be attributed to the permeability and porosity of glass ionomers. (J. W. Nicholson and B. Czarnecka, "The release of ions by compomers under neutral and acidic conditions," Journal of Oral Rehabilitation, vol. 31, no. 7, pp. 665-670, 2004). Being permeable, glass ionomers readily uptake storage media (A. J. Preston, S. M. Higham, E. A. Agalamanyi, and L. H. Mair, "Fluoride recharge of aesthetic dental materials," Journal of Oral Rehabilitation, vol. 26, no. 12, pp. 936-940, 1999). While this enhances fluoride release and fluoride recharge (X. Xu and J. O. Burgess, "Compressive strength, fluoride release and recharge of fluoride-releasing materials," Biomaterials, vol. 24, no. 14, pp. 2451-2461, 2003), it can also cause breakdown of the non-silanized glass fillers within glass ionomers and produce a reduction in mechanical properties. This degradation, as well as the absolute values of glass ionomer physical properties, limits the use of glass ionomers in load bearing restorations.

Also, FRRMs cannot be treated with high temperature heat treatment. This is due to the fact that currently available FRRMs as a form of RMGI (resin-modified glass-ionomer) use FAS (Fluoroaluminosilicat) glass as a filler in a resin matrix. Dental resins that form a matrix to grab the glass are very susceptible to and are not compatible with high temperature heat treatment (usually over 800° C.) that most crowns require in the final processing stage for a desirable strength.

For these reasons and limitations, FRRMs and CIMs have not been used in fabricating dental crowns. It has been recognized by the present inventors that it would be advantages if crowns could release fluoride ions, and/or calcium ions, and/or phosphate ions to inhibit the caries in the adjacent tooth surface and still strong enough to bear the excessive occlusion bite force.

CIMs and FRRMs as a form of a composite have been used, in relation to a permanent dental crown, only as a seating adhesive, benefiting the tooth preparation margin area only, thus having a very limited effect.

Caries are formed mainly at three locations of a tooth; between the teeth, the deep occlusal area, and around the gingiva (or gumline). Of these, caries between the teeth are the most frequently found for adults.

Based on these limitations and problems mentioned above, there is a need for an indirect crown that 1) has caries inhibiting capabilities for between the teeth, 2) has a high flexural strength that comes ultimately from the first material in a stress-bearing area over at least 100 Mpa, preferably over 150 Mpa as in the first material being a glass polymer crown, preferably over 200 Mpa as in the first material being a nano ceramic crown, preferably over 400 Mpa as in the first material being a glass ceramic crown, preferably over 1,000 Mpa as in the first material being a zirconia crown, 3) can withstand high temperature, preferably over 300° C., heat treatment in post processing for strengthening purposes.

In one aspect, one way for adjacent natural teeth to be re-mineralized from such a dental crown over long periods of time is to make a substantial amount of open space in a non-load-bearing area of a dental crown, preferably on or around the mesial and/or distal area and fill this area with a substantial amount of composite form of CIMs, FRRMs. By providing a dental crown with an open space which receives a caries inhibiting material at a later stage, a crown becomes caries inhibiting and re-mineralizing.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 6a is a side schematic view of the sectioned dental stone model with the precursor crown of FIG. 3 shown with a broad contact area on a distal area and having an open contact point on a mesial area between corresponding adjacent teeth due to the open spaces and before the second caries inhibiting material fills the open spaces;

FIG. 6b is a distal view or end view of the precursor crown of FIG. 3 showing the open space within the contact area;

FIG. 6c is a buccal view of the precursor crown of FIG. 3;

FIG. 6d is a cross-sectional bottom view of the precursor crown of FIG. 3, taken along line 6d of FIG. 6a;

FIG. 7a, is a side view of the sectioned dental stone model with the precursor crown of FIG. 3 shown with a broad contact area on the distal area and having a contact point on the mesial area between the teeth after the second caries inhibiting material is filled in the open spaces;

FIG. 7b is a distal view or end view of the precursor crown of FIG. 3 showing the open space and the second caries inhibiting material within the contact area;

FIG. 7c is a top view or occlusal view of the precursor crown of FIG. 3;

FIG. 7d is a cross-sectional bottom view of the precursor crown of FIG. 3, taken along line 7d of FIG. 7a;

FIG. 8a is a side schematic view of the sectioned dental stone model with the precursor crown of FIG. 3 shown with an open contact on the mesial and distal sides between corresponding adjacent teeth due to the open spaces and before the second caries inhibiting material fills the open spaces;

FIG. 8b is a mesial view or end view of the precursor crown of FIG. 3;

FIG. 8c is a mesial view or end view of the precursor crown of FIG. 3;

FIG. 8d is an occlusal view of the precursor crown of FIG. 3;

FIG. 8e is an occlusal view of the precursor crown of FIG. 3;

FIG. 9a, is a side view of the sectioned dental stone model with the precursor crown of FIG. 3 shown with a contact point on the mesial and the distal sides between the teeth after the second caries inhibiting material is filled in the open spaces;

FIG. 9b is a mesial view of the precursor crown of FIG. 3;

FIG. 9c is a mesial view of the precursor crown of FIG. 3;

FIG. 9d is a top view or occlusal view of the precursor crown of FIG. 3;

FIG. 9e is a bottom view of the precursor crown of FIG. 3;

FIGS. 10a and 10b are occlusal and mesial views, respectively, of precursor crown of FIG. 3 before filling the open spaces with the second caries inhibiting material;

FIGS. 10c and 10d are occlusal and mesial views, respectively, of the precursor crown of FIG. 3 after filling the open spaces with the second caries inhibiting material;

FIGS. 10e and 10f are occlusal and mesial views, respectively, of precursor crown of FIG. 3 before filling the open spaces with the second caries inhibiting material;

FIGS. 10g and 10h are occlusal and mesial views, respectively, of the precursor crown of FIG. 3 after filling the open spaces with the second caries inhibiting material;

FIGS. 11a and 11b are occlusal and mesial views, respectively, of the precursor crown and having open spaces around the mesial and distal area at the mesio-buccal, mesio-lingual, disto-buccal, and disto-lingual before filling the open spaces with the second caries inhibiting material;

FIGS. 11c and 11d are occlusal and mesial views, respectively, of the precursor crown after filling the open spaces with the second caries inhibiting material;

FIGS. 12a and 12b are occlusal and mesial views, respectively, of the precursor crown before filling the open spaces with the second caries inhibiting material;

FIGS. 12c and 12d are occlusal and mesial views, respectively, of the precursor crown after filling the open spaces with the second caries inhibiting material;

FIG. 12f showing a buccal contour substantially the same as the final crown; FIG. 12g showing a buccal contour proportionally larger than the final crown; FIG. 12h showing a buccal contour at least half the same as the final crown;

FIG. 13b showing a perimeter of a pocket or open space surrounding or circumscribing a contact area (i.e. an open space perimeter is outside and encompasses a contact area perimeter); FIG. 13c showing a perimeter of a pocket or open space partially inside and partially outside a contact area (i.e. an open space perimeter is partially inside and partially outside a contact area perimeter); FIG. 13d showing pockets or open spaces outside the contact area (i.e. an open space perimeter is completely outside a contact area perimeter);

FIG. 14b showing a perimeter of a pocket or open space surrounding or circumscribing a contact area (i.e. an open space perimeter is outside and encompasses a contact area perimeter); FIG. 14c showing a perimeter of a pocket or open space partially inside and partially outside a contact area (i.e. an open space perimeter is partially inside and partially outside a contact area perimeter); FIG. 14d showing pockets or open spaces outside the contact area (i.e. an open space perimeter is completely outside a contact area perimeter);

FIG. 15b showing a contact point on the open space perimeter; and FIG. 15c showing a contact point outside the open space perimeter;

FIG. 16b showing a contact point on the open space perimeter; and FIG. 16c showing a contact point outside the open space perimeter;

FIGS. 19a, 20a and 21a are buccal side views of the precursor crown with different shapes of open spaces before being filled with the second material or caries inhibiting material; with FIG. 19a showing an open space with an oval shape; FIG. 20a showing an open space with rectilinear sides and bottom, and opening towards the occlusal side; and FIG. 21a showing an open space with rectilinear sides and top, and opening towards the bottom side;

FIGS. 19b, 20b and 21b are buccal side views of the final crown with different shapes of open spaces after being filled with the second material or caries inhibiting material;

FIGS. 19c, 20c and 21c are top views of the final crown with different shapes of open spaces after being filled with the second material or caries inhibiting material;

FIGS. 19d, 20d and 21d are mesial side views of the final crown with different shapes of open spaces after being filled with the second material or caries inhibiting material;

FIG. 26 is a side schematic view of the precursor crown with a dental bur forming the pocket or open space;

FIG. 27 is a side schematic view of the final crown with the pocket or open space filled with a second material or caries inhibiting material;

FIGS. 28, 29 and 30 are occlusal, mesial side, and detailed views of the final crown of FIG. 27;

FIGS. 31a, 32a and 33a are top or occlusal views of the precursor crown with pockets or open spaces, namely holes extending from an exterior surface to a concavity before filling with the second material or caries inhibiting material;

FIGS. 31b, 32b and 33b are mesial side views of the precursor crown with pockets or open spaces, namely holes extending from an exterior surface to a concavity before filling with the second material or caries inhibiting material;

FIGS. 31c, 32c and 33c are top or occlusal views of the final crown with pockets or open spaces, namely holes extending from an exterior surface to a concavity after filling with the second material or caries inhibiting material;

FIGS. 31d, 32d and 33d are mesial side views of the final crown with pockets or open spaces, namely holes extending from an exterior surface to a concavity after filling with the second material of the caries inhibiting material;

FIGS. 31e and 31f are top or occlusal and mesial side views, respectively, of the precursor crown with pockets or open spaces, namely holes, extending from an exterior surface to a concavity before filling with the second material;

FIGS. 31g and 31h are top or occlusal and mesial side views, respectively, of the final crown with pockets or open spaces, namely hoes extending from an exterior surface to a concavity after filling with the second material;

FIGS. 36a-37b are schematic views showing test results of the caries inhibiting capability of the final crown and the average percentage change in the caries area of the adjacent tooth;

FIG. 39 is a flowchart showing another method for making a dental prosthesis or restoration, such as a crown; and FIG. 40 is a flowchart showing another method for making a dental prosthesis or restoration, such as a crown.

Figure 1A:
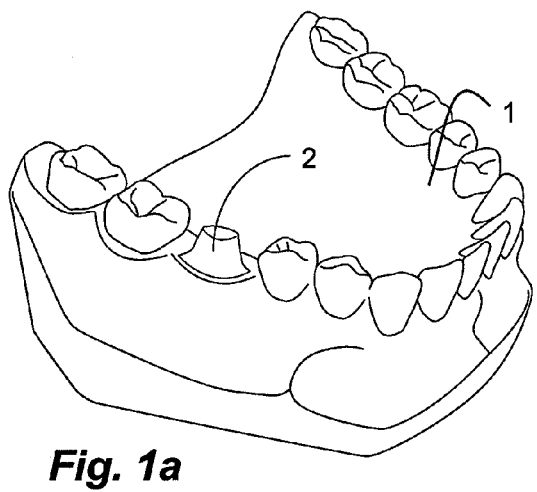
FIG. 1a is a perspective view of a dental stone model representing the patient's teeth including a prepared tooth that has been cut to receive a dental prosthesis or restoration.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definition of the Terms

Bioactive material: Dental bioactive material means a non-inert restorative material. A bioactive material can release agents like calcium ions, phosphate ions, fluoride ions, silver ions, zinc ions, iodine, chlorhexidine, and other agents to help a tooth's hard tissue remineralize or be protected from being demineralized. Most dental restorative materials are inert with respect to biological tissues (soft and hard) of the tooth.

Caries and/or cavities: the demineralization or dissolution of tooth mineral.

Demineralization: the loss of mineral in tooth structure, resulting in mineral-deficient lesions. The terms "remineralization", "mineralization" and similar terms mean the formation of solid inorganic structures similar to the mineral in natural teeth.

Direct restoration: a restoration made directly in the patient's mouth by the dentist, not by a dental technician outside of the mouth.

Indirect restoration: a restoration made outside of the patients mouth, usually in the dental laboratory.

Crown: an indirect dental restoration with mesial side, buccal, distal side, lingual and occlusal walls connected to form a concavity therein, and the concavity contacting a prepared tooth cut by a dentist, or an implant abutment. Inlays and onlays are not dental crowns since they do not have all five cap walls consisting of mesial side, buccal, distal side, lingual and occlusal walls. A bridge is a multiple tooth dental crown. The filling of material onto the human tooth (a "filling") is done directly inside the patient's mouth and is not a dental crown. The term crown is used herein to include bridge for simplicity of discussion. In addition, the terms dental prosthesis, dental restoration, final restoration, restoration crown, restoration bridge, crown and bridge are used interchangeably herein.

Precursor crown: refers to a crown made of a first material having an open space or pocket not filled with a second material, or a caries inhibiting material with caries inhibiting capabilities. A precursor crown becomes a final crown after it receives a second material or caries inhibiting material in the pockets or open spaces. A crown can be a precursor crown if it has not received a second material or caries inhibiting material. The terms precursor crown, precursor bridge and precursor restoration are used interchangeably herein.

Mesial or mesial side: Situated toward the middle of the front of the jaw along the curve of the dental arch. The direction towards the anterior midline in a dental arch, as opposed to distal or distal side, which refers to the direction towards the last tooth in each quadrant. Each tooth can be described as having a mesial surface and, for posterior teeth, a mesiobuccal (MB) and a mesiolingual (ML) corner or cusp. Both mesiobuccal and mesiolingual are regarded as a part of the mesial area of a crown throughout the application of this invention.

Distal or distal side: Situated farthest from the middle and front of the jaw towards the throat. The opposite side of mesial side. The direction towards the last tooth in each quadrant of a dental arch, as opposed to mesial or mesial side, which refers to the direction towards the anterior midline. Each tooth can be described as having a distal surface and, for posterior teeth, a distobuccal (DB) and a distolingual (DL) corner or cusp. Both distobuccal and distolingual are regarded as a part of the distal area of a crown throughout the application of this invention.

Lingual side: a side of a crown the tongue touches in the closed bite position. The side of a tooth adjacent to (or the direction towards) the tongue, as opposed to buccal, labial, or facial which refer to the side of a tooth adjacent to (or the direction towards) the inside of the cheek or lips, respectively.

Buccal side: a side of a crown the cheek touches in the closed bite position. The opposite side of the lingual side. The side of a tooth that is adjacent to (or the direction towards) the inside of the cheek, as opposed to lingual or palatal, which refer to the side of a tooth adjacent to (or the direction towards) the tongue or palate, respectively. Although technically referring only to posterior teeth (where the cheeks are present instead of lips, use of this term may extend to all teeth, anterior and posterior), this term may be employed to describe the facial surface of (or directions in relation to) anterior teeth as well.

Labial: The side of a tooth that is adjacent to (or the direction towards) the inside of the lip, as opposed to lingual or palatal, which refer to the side of a tooth adjacent to (or the direction towards) the tongue or palate, respectively. Although technically referring only to anterior teeth (where the lips are present instead of cheeks), use of this term may extend to all teeth, anterior and posterior.

Occlusal side: top surface of a crown. The surface of a crown that opposes the opposing arch. The occlusal wall of a crown contacts the other occlusal surface of the tooth of the opposing arch in closed bite position.

Contact area and/or contact point: mesial and/or distal area and/or point where the indirect crown restoration directly abuts with the adjacent tooth surface. The shape of the area can be various; irregular, oval, thick linear, thin linear, etc. The size can also vary as little as from 0.1 mm$^2$ to as large as about 10 mm$^2$.

Contact area perimeter: when viewed from either mesial or distal side of a tooth, the perimeter of contact area means a circumferential path around the contact area.

Open space: A 3-dimensional and substantial pit, pocket, concavity, hole, undercut, dent, recessed area that can be on or around at least one of the mesial and/or distal areas of the crown, creating an incomplete mesial and/or distal contour, but at the same time creating the same or substantially the same or proportionately the same buccal contour when compared to the finished final crown. The open space can be a pocket formed as an indentation into the restoration or crown. The pocket or open space can be concave. In addition, the pocket or open space can have an undercut with a larger interior and a smaller opening thereto. The open space can be a hole extending through a wall of the restoration or crown from an exterior surface to a concavity therein that receives a prepared or cut tooth, or an implant abutment. The open space can extend into the otherwise occurring surface of the restoration or crown. A small open space can also be made on either the buccal area or lingual area or both.

Open space perimeter: when viewed from either the mesial or distal side of a crown, the perimeter of the open space of a crown means a circumferential and generally closed path around the open space. The open space perimeter can be wholly or entirely on or around the mesial and/or distal side wall.

Open contact: A relationship between immediately adjacent teeth (or crown and adjacent tooth) in which there exists a gap or distance. The gap or distance can be as little as 0.01 mm and as wide as 1 mm. If an open space exists inside the contact area perimeter, this is also an open contact. The open space or pocket in the precursor crown could cause an open contact relationship with an adjacent tooth.

Closed contact: A relationship between immediately adjacent teeth (or crown and adjacent tooth) in which there exists no gap or distance. An open contact of the current crown can receive a second material or a caries inhibiting material in the open space or pocket, and the open contact relationship can be brought to the closed contact relationship. The second material in the open space or pocket of the precursor crown or final crown can abut to an adjacent tooth, defining a closed contact relationship.

Margin line: the "margin" 17 of a cut tooth 2 (FIG. 3) or an implant abutment 2' (FIG. 2d) is a circumferential line created after the tooth preparation, or manufactured on the implant abutment. The margin line of a cut tooth exists either slightly over (supra-gingival), or along, or slightly below (sub-gingival) the gum line. The crown margin line is a circumferential line corresponding to the margin line of a cut tooth.

Preparation, prep, cut(ting), grind(ing) of a tooth can be interchangeably used to mean grind away at least a portion of a tooth to make a restoration.

Hardenable, cureable, polymerization and related terms refer to a paste-like or liquid-like material being able to harden and form a solid. The term "monomer" refers to a liquid that can be hardened to form a polymer.

Glaze: A layer or coating of a vitreous substance which has been fused to a ceramic crown through firing at a temperature of 500-1,100° C.

Glazing: High temperature firing of the crown for a shiny or polished effect.

As used herein, "a" or "an" means "at least one" or "one or more" unless otherwise indicated.

For a better understanding of the present invention, together with other and further objects, reference is made to the following description, taken in conjunction with the accompanying drawings, and its scope will be pointed out in the appended claims.

Description

The present invention provides a method for making a dental prosthesis or restoration, such as a crown or bridge, that maintains adequate strength and aesthetics, while providing a second material in an open space or pocket. The description will focus on a crown with the understanding that such description applies to a bridge as well. The method includes forming a precursor crown based on a scan, mold, or model of the patient's teeth. A patient's tooth may be cut to form a prepared or cut tooth to receive the crown. Or the crown can be disposed on an implant with an implant abutment. The crown is formed with a concavity therein to receive the prepared tooth or implant abutment. In addition, the precursor crown can be formed with a buccal contour substantially the same as a final buccal contour. Thus, the buccal contour of the precursor crown can have the same size, shape and contour as the final crown, or can be sized proportionally larger to shrink to the final size after heat hardening. The precursor crown can comprise a first dental restoration material, which can be pre-hardened, or subsequently heat hardened. The precursor crown can be cut or milled from a block of the first dental restoration material. In addition, one or more open spaces or pockets can be formed in the precursor crown in or about the mesial and/or distal side walls. When the precursor crown has substantially the same strength as the final crown, and a buccal contour substantially the same as the final crown, a second material, different from the first material of the precursor crown, can be filled and secured into the open spaces or pockets. In one aspect, the second material can have a lower flexural strength and/or a lower temperature tolerance than the first material. In another aspect, the second material can be a caries inhibiting material. The first material can be or can comprise zirconia, ceramic, or metal. The precursor crown can have substantially the same strength as the final crown by: 1) being heat hardened after milling (such as with zirconia); or 2) being pre-hardened (such as with ceramic or metal); or 3) being pre-hardened and heat treated (such as with metal with a ceramic overlay on the buccal wall). The precursor crown can have a buccal contour substantially the same as the final crown by being the same shape, size and contour by: 1) being milled proportionally larger than the final crown, and then being shrunk during heat hardening (such as with zirconia); 2) being milled the same shape, size and contour from pre-hardened material (such as with ceramic); or 3) being milled from a pre-hardened material and having an overlay on the buccal wall of a different material that is glazed and/or polished (such as with a metal with a ceramic overlay on the buccal wall). The precursor crown with the second material disposed in and filling the open space or pocket in the mesial and/or distal side walls forms a final crown that can be mounted on the prepared tooth or implant abutment.

Referring to FIGS. 1a-40, a dental prosthesis or restoration is shown, such as a crown 5 (FIGS. 1a-24b and 26-40) or bridge 80 (FIG. 25) restoration, and a method for making such a prosthesis or restoration is shown, in accordance with an exemplary embodiment of the invention. In one aspect, the crown can be modeled digitally based on a digitized scan of the patient's teeth, or a digitized scan of a model of the patient's teeth, or a digitized scan of a mold of the patient's teeth. In another aspect, the crown can be made based on a physical model or dental stone model 1 of the patient's teeth. The model 1 can be segmented to create a working die 4. The patient's tooth can be cut while in the patient's mouth to form a prepared or cut tooth. The model (physical or digital) can include the prepared or cut tooth 2 (with reference number 2 used herein to refer to both a cut tooth and a model of the cut tooth). The crown 5 can be formed outside of the patient's mouth based on the model (again physical or digital).

The dental prosthesis or restoration, or the dental crown 5 or bridge 80 restoration, can have occlusal 15, mesial side 11, buccal 14, distal side 12, and lingual walls 13. The buccal wall 14 can be adjacent a patient's cheek. The lingual wall 13 can be adjacent a patient's tongue. The occlusal wall 15 can face an opposing tooth. The mesial and the distal side walls 11 and 12 can each face a different adjacent tooth 8 (with reference number 8 used herein to refer to both the adjacent teeth and a model of the adjacent teeth). The walls are connected to define a concavity 16 therein to receive and match the prepared tooth 2 or an implant abutment 2'.

In one aspect, the method of making the crown 5 (or bridge 80), can include a plurality of sequential steps. In another aspect, the method can include various steps in any order. The method includes receiving a margin line information regarding the margin line 17 of the prepared tooth 2 or the implant abutment 2'.

Then (after receiving the margin line information), a precursor crown 5' or bridge restoration is formed outside of a patient's mouth with a first restorative material 6. Forming the precursor crown 5' can include creating a restoration margin line 18 corresponding with the margin line information of the prepared tooth 2 or the implant abutment 2'. In addition, the precursor crown 5' can be formed to have the occlusal 15, mesial side 11, buccal 14, distal side 12, and lingual walls 13. The precursor crown 5' can also be formed to have forming a concavity 16 opposite the occlusal wall 15 and between the walls to receive and match the prepared tooth 2 or the implant abutment 2'. In addition, forming the precursor crown 5' can include creating a buccal contour on the buccal wall 14 of the precursor crown 5' substantially the same as a buccal contour on a final crown 5 or bridge restoration. Furthermore, forming the precursor crown 5' can include creating an open space or pocket 9 and/or 10. The open space or pocket can have an open space perimeter 30 on or around at least one of the mesial side wall 11 or the distal side wall 12.

Then (after forming the precursor crown 5'), a second material 7, different from the first restorative material, is filled and secured inside the open space(s) or pocket(s) 9 and/or 10 of the precursor crown 5' or bridge restoration while outside the patient's mouth. The precursor crown 5' or bridge restoration has a strength substantially equivalent to the final crown 5 or bridge 80 restoration, prior to filling and securing the second material. In addition, the buccal contour on the buccal wall 14 is substantially the same as the buccal contour on the final crown 5 or bridge restoration, prior to filling and securing the second material. The precursor crown 5' with the second material 7 disposed in the open space(s) or pocket(s) defines the final crown 5. In one aspect, the method can further comprise contouring an exposed portion of the second material 7. In one aspect, an entire volume of the open space or pocket 9 and/or 10 can be filled with the second material 7. In another aspect, the second material 7 can have a greater volume than a volume of the open space or pocket 9 and/or 10, so that the second material 7 extends outwardly beyond a surface of the mesial and/or the distal side walls 11 and/or 12 of the precursor crown 5' or bridge restoration.

In one aspect, the precursor crown 5 or bridge restoration can be formed so that it would have a closed contact relationship 21 (FIG. 9a) with a corresponding adjacent tooth 8 when finished. The open space or pocket 9 and/or 10 can be created in the precursor crown 5' so that it would have an open contact relationship 22 (FIG. 8a) with respect to the corresponding adjacent tooth 8 due to the open space or pocket. The open space or pocket 9 and/or 10 can be filled with the second material to have a closed contact relationship 21 with the corresponding adjacent tooth 8 when the crown 5 or bridge restoration is installed on the prepared tooth 2 or the implant abutment 2'.

As described above, the second material 7 is disposed in the precursor crown 5' or bridge restoration after the precursor crown 5' has a strength substantially equivalent to the final crown 5 or bridge 80 restoration. In one aspect, the precursor crown 5' or bridge restoration can be heat hardened when or if the first material 6 does not have a strength substantially equivalent to a final restoration; prior to filling and securing the second material 7 inside the open space or pocket 9 and/or 10 of the precursor crown 5' or bridge restoration. The precursor crown 5' or bridge restoration can be heat hardened with the buccal contour and the open space or pocket 9 and/or 10, to define a hardened precursor crown or bridge restoration, prior to filling and securing the second material 7. In another aspect, the precursor crown 5' or bridge restoration can be formed from the first material 6 that is pre-hardened, and has a strength substantially equivalent to a final crown 5 or bridge restoration.

As described above, the second material 7 is disposed in the precursor crown 5' or bridge restoration after the buccal contour on the buccal wall 14 is substantially the same as the buccal contour on the final crown 5 or bridge restoration. Thus, the buccal contour on the buccal wall 14 can be formed substantially the same as a buccal contour on a final crown or bridge restoration, prior to filling and securing the second material 7 inside the open space or pocket 9 and/or 10 of the precursor crown 5' or bridge restoration.

In another aspect, at least the buccal contour of the buccal wall 14 of the precursor crown 5' or bridge restoration can be glazed, or polished, or both, prior to filling and securing the second material 7 in the open space or pocket 9 and/or 10.

Thus, forming the precursor crown 5' or bridge restoration can comprise creating a substantially complete buccal contour on the buccal wall 14, but an incomplete mesial contour on the mesial side wall 11, or an incomplete distal contour on the distal side wall 12, or both. Thus, the buccal contour on the buccal wall 14 can be proportional to a final buccal contour on the buccal wall 14 of a final crown 5 or bridge restoration. In one aspect, forming the precursor crown can comprise the buccal contour of the precursor crown 5' being substantially the same, but proportionately larger, than the buccal contour of the final crown 5'. The buccal contour can shrink or reduce in size to the final buccal contour after heat hardening. In another aspect, the buccal contour of the precursor crown 5' can be substantially the same, and substantially the same size, as the buccal contour of the final crown, particularly if the first material is pre-hardened.

In one aspect, the first material 6 can be inert, and the second material 7 can be bioactive. In one aspect, the first material 6 can have a higher flexural strength or a higher temperature tolerance than the second material 7. In one aspect, the first material 6 can comprise at least one of: dental porcelain, zirconia, glass ceramic, composite material, ceramic-composite hybrid material, resin composite, metal, CAD CAM restorative material, CAD CAM dental blocks; or combinations thereof. In one aspect, the second material 7 can comprise at least one of: calcium ions, phosphate ions, fluoride ions, titania ions, iodine, chlorhexidine, glass ionomer, resin-modified glass ionomer, compomers, calcium phosphate, tri-calcium phosphate (TCP), tetracalcium phosphate (TTCP), dicalcium phosphate anhydrous (DCPA), amorphous calcium phosphate (ACP), calcium and phosphate fillers that release calcium and phosphate ions, silver ions, nano silver particles, silver zeolite, or combinations thereof.

As described above, forming the precursor crown 5' or bridge restoration comprises creating an open space or pocket 9 and/or 10 with an open space perimeter 30. In one aspect, an undercut 90 (FIGS. 26-29) into the precursor crown 5' or bridge restoration and under the open space perimeter 30 can further be created.

In one aspect, filling and securing the second material 7 can further comprise contouring an exposed portion of the second material 7 to be flush with an exterior surface of the precursor crown 5' or bridge restoration surrounding the second material.

In addition, the method can comprise seating and securing the final crown 5 or bridge restoration on the prepared tooth 2 or implant abutment 2' inside the patient's mouth. The second material 7 can have a closed contact relationship 21 (FIG. 9a) with the corresponding adjacent tooth 8.

As described above, the precursor crown 5' can have an open space perimeter 30. In one aspect, the open space perimeter 30 can be inside a contact area perimeter 25 defined between the final crown 5 or bridge restoration and the adjacent abutting tooth 8. In another aspect, the open space perimeter 30 is outside and encompasses a contact area perimeter 25 defined between the final crown 5 or bridge restoration and the adjacent abutting tooth 8. In another aspect, the open space perimeter 30 is partially inside and partially outside 25 a contact area perimeter defined between the final crown 5 or bridge restoration and the adjacent abutting tooth 8. In another aspect, the open space perimeter 30 is completely outside a contact area perimeter 25 defined between the final crown 5 or bridge restoration and the adjacent abutting tooth 8.

As described above, the method for the dental restoration or crown 5 can comprise various steps without necessarily requiring sequential steps. In addition, the method can be configured for use with a first dental restoration material 6 that is heat hardened after milling the precursor crown. Thus, a proportionally larger precursor crown can be milled from the first material or block thereof; then heat hardened to harden the material and precursor crown, and thus shrink the precursor crown to the size of the final crown. For example, the first material can be or can comprise zirconia. The method can comprise forming a precursor restoration or crown 5' from a first restorative material 6 to have occlusal 15, mesial side 11, buccal 14, distal side 12, and lingual 13 walls. A concavity 16 can be formed opposite the occlusal wall 15 and between the walls to receive and match the prepared tooth 2 or the implant abutment 2'. The buccal wall 14 can be contoured to have substantially a desired final contour, the same as the final contour of the final crown 5. At least one pocket 9 and/or 10 can be formed in an exterior of at least one of the mesial side wall 11 or the distal side wall 12. The precursor restoration or crown 5' can be heat hardened, defining a hardened precursor restoration. A second material 7, different than the first material, can be disposed and secured in the at least one pocket 9 and/or 10 of the hardened precursor restoration after final heat hardening. The second material 7 can have an exposed exterior surface.

In addition, the method can comprise receiving a margin line information (of the margin line 17) of the prepared tooth 2 or the implant abutment 2'. A precursor restoration or crown 5' can be formed from a first restorative material 6 outside of a patient's mouth, and to have occlusal 15, mesial side 11, buccal 14, distal side 12, and lingual 13 walls. A restoration margin line 18 can be created corresponding with the margin line information of the prepared tooth 2 or the implant abutment 2'. A concavity 16 can be formed opposite the occlusal wall 15 and between the walls to receive and match the prepared tooth 2 or the implant abutment 2'. The buccal wall 14 can be contoured to have substantially a desired final contour, the same as the final contour of the final crown 5. At least one pocket 9 and/or 10 can be formed in an exterior of at least one of the mesial side wall 11 or the distal side wall 12 that would have an open contact relationship 22 (FIG. 8a), after final heat hardening, with respect to the corresponding adjacent tooth 8 due to the at least one pocket 9 and/or 10. The precursor restoration can be heat hardened, defining a hardened precursor restoration. A second material 7, different than the first material, can be disposed and secured in the at least one pocket 9 and/or 10 of the hardened precursor restoration after heat hardening, and while outside the patient's mouth, defining a final restoration 5. The second material 7 can have an exposed exterior surface. In addition, the first material 6 can have a higher flexural strength and/or a higher temperature tolerance than the second material 7. Thus, the first material 6 can be head hardened prior to disposing the second material 7 in the pockets. The final restoration 5 can be seated and secured on the prepared tooth 2 or implant abutment 2' inside the patient's mouth. In addition, the final crown 5 and/or the second material 7 can have a closed contact relationship 21 (FIG. 9a) with the corresponding adjacent tooth 8.

Furthermore, the method can comprise forming a precursor restoration or crown 5' from a first restorative material 6 to have occlusal 15, mesial side 11, buccal 14, distal side 12, and lingual 13 walls. A concavity 16 can be formed opposite the occlusal wall 15 and between the walls to receive and match the prepared tooth 2 or the implant abutment 2'. The buccal wall 14 can be contoured to have substantially a desired final contour, the same as the final contour of the final crown 5. At least one pocket 9 and/or 10 can be formed in an exterior of at least one of the mesial side wall 11 or the distal side wall 12. The precursor restoration 5' can be heat hardened when or if the first material 6 does not have a strength substantially equivalent to a final restoration or final crown 5, such as with zirconia. A second material 7, different than the first material, can be disposed and secured in the at least one pocket 9 and/or 10 of the precursor restoration or crown 5', and with the precursor restoration or crown having a desired contour on the buccal wall substantially the same as that of the final restoration or crown 5, and/or a strength substantially equivalent to a final restoration or crown 5.

As discussed above, in one aspect, the second material 7 can be or can comprise a caries inhibiting material (such as fluoride, calcium, phosphate, silver, copper) in a mass or bulk form separately applied to the side of a crown 5 in an open space 9 and/or 10 area, so the natural tooth 8 adjacent to the crown can have a reduced possibility of caries incidence. That is, unrestored mesial/distal surfaces of the adjacent teeth 8 contacting the caries inhibiting material, such as a fluoride releasing material, may exhibit a lower incidence of caries compared to a surfaces contacting a regular crown. Thus, the crown 5 or caries inhibiting material can deliver anti-caries fluoride ions, for example, to the adjacent tooth 8 surfaces to inhibit the progression of caries in the area of such application. Caries inhibiting material filled inside the open space can be substantially a mass or bulk, making it possible to have a sustained release over a long period of time from the reservoir of rechargeable fluoride material, for example, when used with fluoridated dentifrices.

In addition, the crown 5 can have a high flexural strength from the primary frame of the first material 6, such as anywhere between 100-1,400 Mpa, compared to the second material 7, such as current fluoride releasing restorative materials that exhibit only 20-100 Mpa when used alone, exhibiting significantly much higher flexural strength, and at the same time, having a caries inhibiting capability.

In addition, the first restorative material 6 of the crown 5 can be made to withstand high temperature heat treatment, preferably over 300° C., in post processing for strengthening purposes.

In addition, with the crown 5, the multifactorial disease process of demineralization and caries can be slowed or even stopped before more extensive treatment becomes necessary. Caries inhibition materials implanted in the side of the crown in a significant mass or bulk amount releases fluoride or calcium or phosphate and other agents to impede decay and to repair or remineralize tooth structure that has already started losing minerals.

In addition, the aesthetics of the crown is not compromised at all since the caries inhibiting material is applied on or around the mesial and/or distal side walls 11 and 12 while or after the crown is made with a first material 6 that creates the same or substantially the same buccal contour as the final crown. The mesial and/or distal side of a crown is generally hidden between the teeth and not noticeable, thereby not detracting from the aesthetic aspect of a crown restoration.

The second material 7 can be or can comprise fluoride, for example, that can be released by the crown 5 from the mass or bulk filled in the open space 9 and/or 10 so that the fluoride is constantly present in the mouth, and adjacent the teeth 8. Test results indicated that caries inhibiting material in constant contact with an adjacent incipient carious lesion had the same remineralization capacity as twice-daily brushing with a fluoridated dentifrice.

In addition, the crown 5 can retain the caries inhibiting material, fluoride ions for example, delivered by dentifrices, mouth rinse or topical fluoride treatments at the material surface, and then release these fluoride ions slowly over an extended period of time from the substantial mass or bulk amount of caries inhibiting material in the mesial and/or distal area of open space 9 and/or 10. The open space or pockets 9 and/or 10, and/or the caries inhibiting materials can act as a reservoir of bioactive material directly working toward the adjacent teeth 8 in the prevention, arrest or reversal (remineralization) of incipient carious lesions.

Furthermore, the crown: 1) is able to release the caries inhibiting agent (ions), for example fluoride ions, from the non-load bearing area of the mesial/distal area as a form of a substantial mass or bulk of caries inhibiting material, and 2) still can keep the maximum strength and aesthetics by using two different materials between the overall body area and mesial/distal area of a crown.

Figure 1B:
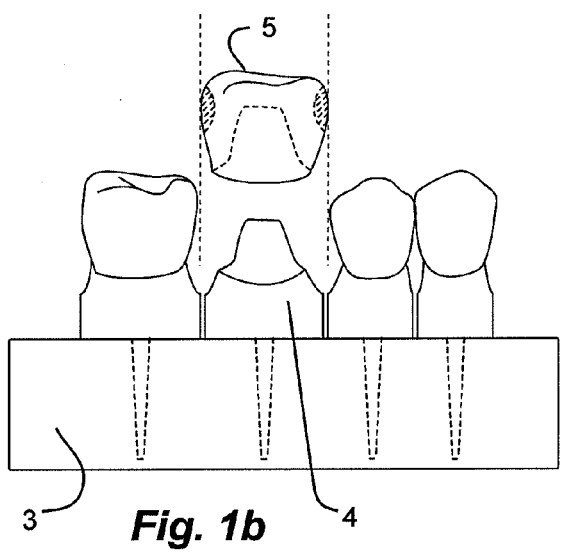
FIG. 1b is an exploded side view of a sectioned dental stone model with a dental prosthesis or restoration, namely a crown, in accordance with an embodiment of the invention.

FIGS. 1a and 1b show a dental stone model 1 with a prepared tooth 2 and an indirect crown 5. In one aspect, after the tooth 2 with caries has been prepared inside the mouth by a dentist, a negative dental silicone impression representing the overall teeth, including prepared tooth 2, is produced and sent to a dental laboratory for an indirect dental crown restoration 5. Dental stone is poured onto the impression to produce a stone model 1. In another aspect, the model 1 can be 3D printed using a CAD/CAM system. This dental model 1 is further sectioned to make working die 4 on a dental base 3.

Small cavities are easily removed by a dentist and treatment is finished directly inside the mouth by filling with a dental cement or other restorative material in the prepared area. This type of restoration is called direct treatment/restoration since the whole process is done by a dentist directly inside the mouth. A direct restoration has some limitations based on the limited intra-oral working space and the restoration is quite weak in its strength since a form of heat treatment that makes a material strong is not possible in the intra-oral environment. Whereas, if the cavity is more serious and the ground tooth area is more significant, the remaining tooth portion needs to be protected, usually by a crown made by a dental laboratory. This type of restoration is referred to as an "indirect restoration". The benefit of the indirect restoration as opposed to a direct restoration is that they are aesthetically superior as it is made outside of the mouth by a skilled dental technician and most of the time heat processing is applied to make the ceramic material exhibit a desired mechanical strength including flexural strength, fracture toughness, etc.

Figure 2A:
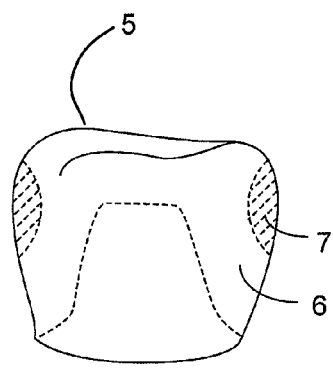
FIG. 2a is a side view of the crown of FIG. 1b having a second material or a second caries inhibiting material filling an open space(s) or a pocket(s) in mesial and/or distal walls or sides of the crown.
Figure 2B:
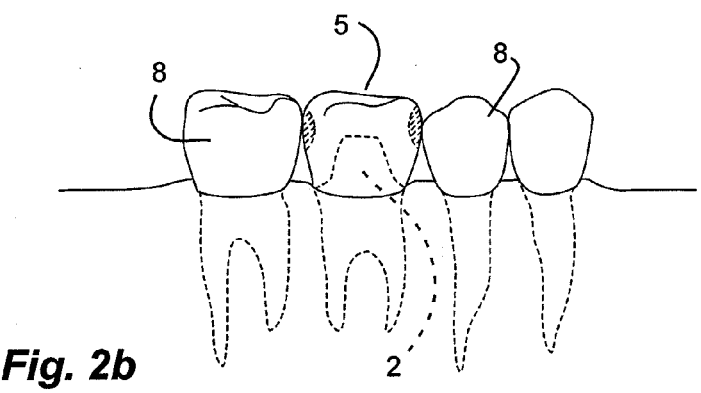
FIG. 2b is a side view of a portion of a patient's mouth with the crown of FIGS. 1b and 2a seated on the prepared tooth.
Figure 2C:
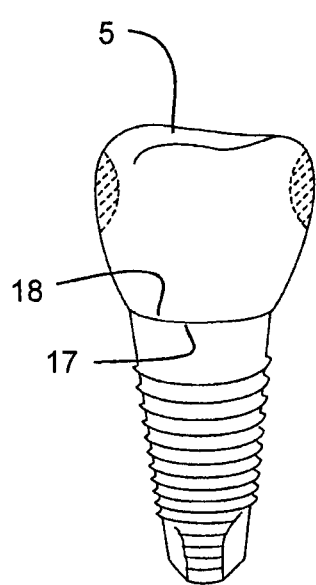
FIG. 2c is a side view of a dental implant with an implant abutment and receiving a dental prosthesis or restoration thereon, namely a crown, in accordance with the invention.
Figure 2D:
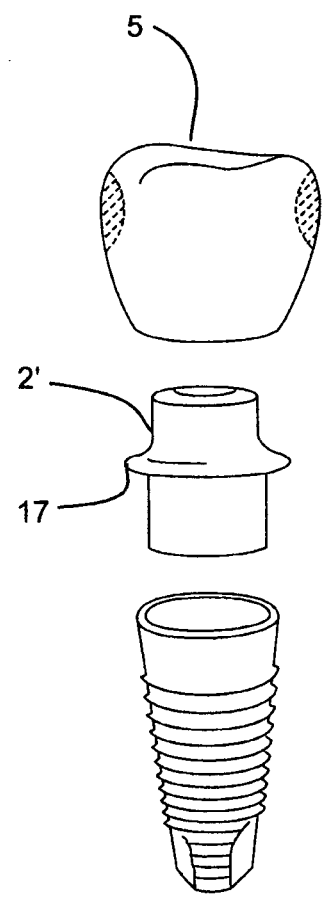
FIG. 2d is an exploded side view of the dental implant with the implant abutment receiving the dental prosthesis or restoration thereon of FIG. 2c.

FIG. 2a shows the indirect restoration crown 5 with the first material 6 substantially constituting the major part of the precursor crown body 5', and the caries inhibiting second material 7 applied on or around at least one of the mesial and distal sides 9 and/or 10 of a crown. After a crown is finished outside the patient's mouth, it is then seated on the patients prepared tooth 2 or implant abutment 2' to abut with the adjacent natural teeth 8 in the patient's mouth. With the insertion of the indirect restoration crown 5 in a fixed way, the treatment is finished and the desired inter-tooth relationship is restored.

Figure 3:
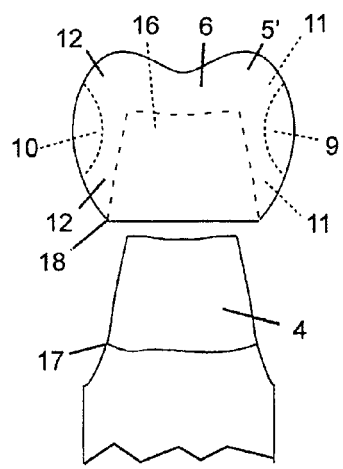
FIG. 3 is an exploded side view or a buccal view of a sectioned dental stone model with a precursor dental restoration, namely a precursor crown, in accordance with an embodiment of the present invention.
Figure 4A:
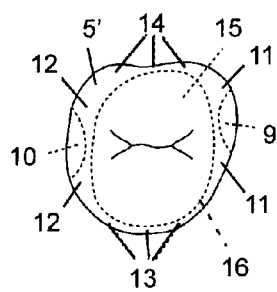
FIG. 4a is a top or an occlusal view of the precursor crown of FIG. 3.
Figure 4B:
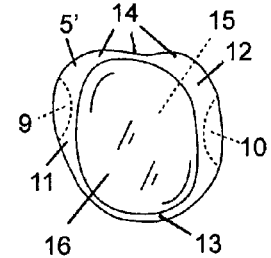
FIG. 4b is a bottom view of the precursor crown of FIG. 3.
Figure 4C:
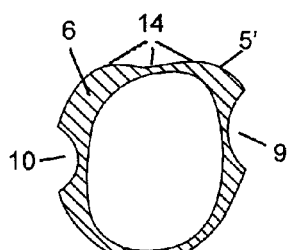
FIG. 4c is a cross-sectional view of the precursor crown of FIG. 3, taken along line 4c of FIG. 3.

FIG. 3 shows a precursor crown 5' of the current inventive crown 5 with an open space or pocket 9 and/or 10 created on or around at least one of the mesial and distal sides walls 9 and/or 10 of the precursor crown 5' to be made on the working die 4. As seen in FIGS. 4a through 4c, a precursor crown 5' generally has five walls, including: mesial side wall 11, distal side wall 12, lingual wall 13 and buccal wall 14, and occlusal wall 15. The mesial wall 11 faces the front teeth and abuts with the distal side of the adjacent tooth. The distal wall 12 faces the direction of the throat and abuts with the mesial side of the adjacent tooth. The lingual wall 13 faces the tongue side in a closed bite position and opposes the buccal wall 14 which faces to the cheek side. The occlusal wall 15 faces the occlusal wall of the opposing tooth of the other arch in a closed bite position. These five walls 11, 12, 13, 14 and 15 are all interconnected to form a clear concavity 16 therein, and the clear concavity receives a prepared tooth 2 cut by a dentist, or an implant abutment 2'.

The first material 6 of the crown 5 or precursor crown 5' can be, but is not limited to, at least one of or a combination of dental porcelain, zirconia, glass ceramic, composite material, ceramic-composite hybrid material, resin composite, metal, CAD CAM restorative material, CAD CAM dental blocks.

As in FIGS. 2a and 7a, the crown 5 uses the second material 7, such as a caries inhibition material, attached into the mesial and/or distal side walls 11 and/or 12 of the first material 6 of a dental crown in a substantial mass or bulk form to work as a reservoir to retain the efficacy of the continued release of ions of bioactive materials.

Method of Creating the Open Space

Figure 5:
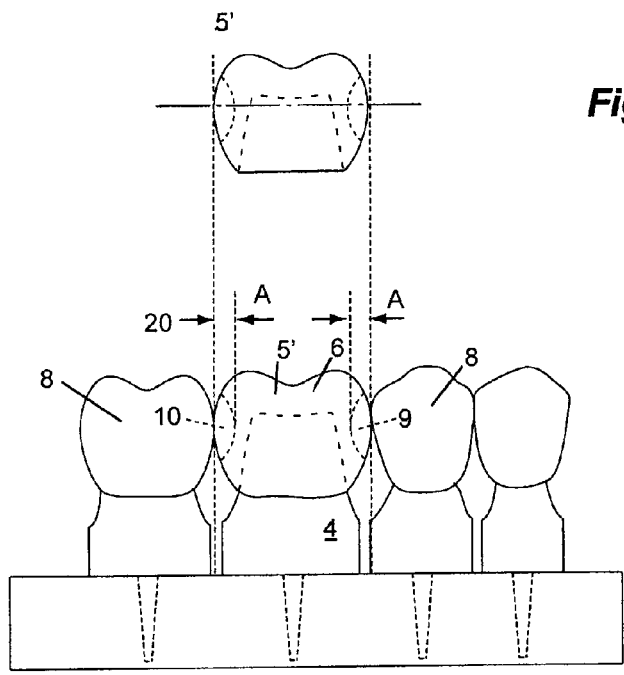
FIG. 5 is a side schematic view of a sectioned dental stone model with the precursor crown of FIG. 3 seated on the sectioned dental stone model to make an indirect crown.
Figure 4E:
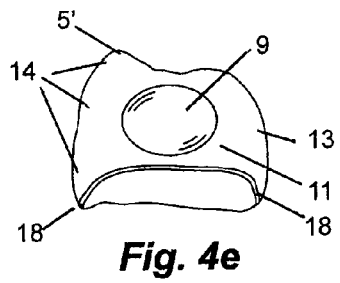
FIG. 4e is a lower perspective view of the precursor crown of FIG. 3.
Figure 4D:
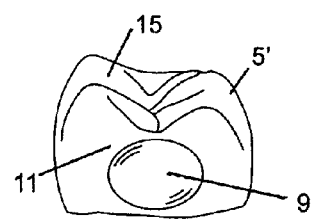
FIG. 4d is an upper perspective view of the precursor crown of FIG. 3.

FIGS. 5 and 6 show a precursor crown 5' of the crown 5 seated on the sectioned working die 4 with at least one open space or pocket 9 and/or 10 to receive a second material 7, such as a caries inhibiting material, in the mesial side wall 11 and/or distal side wall 12 or area of the precursor crown 5'.

The open space 9 and/or 10 can be a substantial pit, pocket, concavity, hole, undercut, dent, or recessed area enough to receive a mass or bulk form of the second material 7, or the caries inhibiting material. The open space can be made typically by grinding the precursor crown 5' with a hand-piece or CAD CAM milling machine. As in FIG. 13c, an open space 9 created on the surface of a crown leaves a perimeter 30 along the edge of the pocket or open space 9. With this open space 9 and its perimeter 30, a substantial 3-dimensional space is created which receives a mass or bulk form of the second material, or the caries inhibiting material.

The precursor crown 5' can be made 1) either as shown in FIG. 6a, to directly contact the adjacent teeth 8 and then subsequently can be manually ground on or around at least one of the mesial 11 and/or distal 12 wall areas of the crown to create an open space 9 and/or 10, or 2) as in FIG. 8, to not touch the adjacent teeth 8 from the beginning, but to have an open contact relationship 22 in which the second material 7, a fluoride releasing material for example, can be applied in this open space 9 and/or 10 to create a closed contact relationship 21 between the teeth. For example, a resin modified glass ionomer or conventional glass ionomer can be used to fill this open space 9 and/or 10.

In addition, the open space or pocket 9 and/or 10 can have a surface or interior that is scarred or roughened to increase surface area and bonding of the second material therein.

General Location of the Open Space

Regarding FIGS. 10, 11 and 12, the open space 9 and/or 10 that receives the second material 7, a fluoride releasing material for example, is generally created on the mesial and/or distal area for maximum effect in relationship with adjacent teeth 8. If an open space is created on the buccal area with a significant volume, and the filling material is applied afterwards, it would detract from the aesthetic aspect of the final crown. If created in the lingual area only, the released fluoride ions would easily be washed away by saliva too soon before it can reach the adjacent teeth and be effective in reducing caries in the adjacent teeth. In some instances, the open space can be created between the mesial and lingual area, called the mesio-lingual area, or between the mesial and buccal area, called the mesio-buccal area, or between the distal and lingual area, called the disto-lingual area, or between the distal and buccal area, called the disto-buccal area, as shown in FIGS. 12i-p. Test results show that the fluoride is incorporated into the hydroxyapatite crystals of the enamel and dentin, over an area of approximately 1-3 mm surrounding the restoration, forming hydroxyfluorapatite. So the closer to the adjacent natural tooth the open space filled with caries inhibiting material is, the better it will work.

It one aspect, the open space be created on the non-load bearing area, avoiding the occlusion area where the opposing tooth directly transfers the biting force since the filling material that is applied to the open space is relatively weak, usually under 100 Mpa in flexural bending strength.

In one aspect, the open space can be located on or around either the mesial 11 or the distal 12 area in an isolated manner, as in FIGS. 10, 11 and 12. If the distal open space 10 and mesial open space 9 is connected along the buccal side 14 of the crown 5 or precursor crown 5' in one continuous recessed manner requiring massive deposit of material, it could be difficult to fill this broad open space (mesial, buccal and distal area) with the second material 7, for example a fluoride releasing filling material, due to the following two reasons: 1) it may cause a lot of inefficiency of having to grind or adjust the entire buccal 14 contour (or surface) to create the final contour, and 2) all the second material, such as a caries inhibiting material in the form of composite, can be composed of resin and releasing material, and resin is not compatible with high temperature heat treatment. All the dental resin could melt over 200° C., and the normal crown making process for a strong crown requires high temperatures, preferably over 200° C. So the buccal 14 contour (or surface) of the precursor crown 5' can be the same contour (or surface) as the final crown 5 before filling the second material 7 into the open space 9 and/or 10.

The second material 7 that can be used to replace the open space of the precursor crown can be in a composite form. Dental composites are composed of a mixture of fillers with a hardenable or polymerizable matrix, for example, an acrylic monomer (also termed resin or dental resin), that is polymerized or hardened to form a composite restoration.

Filling Material—Such as Caries Inhibiting Material

As discussed above, the second material 7 is different from the first material 6. While the first material 6 can be a dental restoration material with greater strength and/or hardness, and greater heat tolerance, compatible with the strength and aesthetical properties desired for a crown; the second material can have a lesser strength and/or lesser heat tolerance, but another desirable characteristic, such as bioactivity, etc. As indicated above, the second material 7 can be or can include a caries inhibiting material. Examples of caries inhibiting materials include, but are not limited to, fluoride ion releasing materials, like glass ionomers, resin-modified ionomers and compomers. The caries inhibiting material can also include calcium or phosphate ion releasing materials. The caries inhibiting material can also include silver, copper, zinc, titania ion releasing materials. The caries inhibiting material can further include gold, palladium, platinum ion releasing materials. It can further include iodine and chlorhexidine.

Glass ionomers, resin-modified glass ionomers and compomers can release fluoride into adjacent tooth structure to combat caries. Glass ionomers refer to dental materials that are based on the acid-base reaction of an aqueous solution of a polycarboxylic acid with an ionleachable, fluoride-containing glass. However, the brittleness and inferior mechanical properties of glass ionomers (flexural strength of 10-20 MPa) have severely limited their use. Resin-modified glass ionomers use resins (for example, 2-hydroxyethyl methacrylate, or HEMA) with the polyacids. The name compomer is derived by combining the two words composite and ionomer, and is intended to suggest a combination of composite and glass-ionomer technology. They are modified in their resin phase by a carboxylic acid monomer, and in their filler phase by the inclusion of an acid-reactive, ion-leachable glass. Resin-modified glass ionomers and compomers are not recommended for use in large, stress-bearing restorations.

The second material or caries inhibiting material inside the open space can further comprise the form of calcium phosphate, tri-calcium phosphate (TCP), tetracalcium phosphate (TTCP), dicalcium phosphate anhydrous (DCPA), amorphous calcium phosphate (ACP), calcium and phosphate fillers that release calcium and phosphate ions.

Other caries inhibiting materials release calcium ($Ca^{2+}$) and phosphate ($PO_4$) ions to form hydroxyapatite (HA), $Ca_{10}(PO_4)_6(OH)_2$, which is the putative mineral in natural teeth (Skrtic et al., J Dent Res 75:1679-1686, 1996; Dickens et al., Dental Material 19:558-566, 2003). These materials are highly promising for remineralizing the carious teeth and helping to prevent the occurrence of caries.

Also silver nanoparticles, either alone or as a composite with other agents, are believed to be effective caries inhibiting restorative agents.

Fluoride releasing materials, as an example of caries inhibiting materials, can be a glass ionomer cement or restorative material. The powder of glass ionomer cement is a calcium fluoroaluminosilicate glass with a formula of SiO2-Al2O3-CaF2-Na3AlF6-AlPO4. The powder is described as an ion-leachable glass.

The benefits of fluoride in reducing the incidence of caries are well established. Thus fluoride releasing materials, as an example of caries inhibiting material, from the crown 5 could be advantageous. Caries inhibiting materials, or fluoride releasing materials, can comprise fillers and polymer resins. Fillers that impart fluoride release include $ZnF_2$, $YbF_2$, rare-earth fluorides, $SnF_2$, $SnF_4$, $ZrF_4$, NaF, $CaF_2$, $YF_3$, and fluoroaluminosilicate glasses.

The fluoride-releasing material, as an example of caries inhibiting material, of the present invention can be naturally occurring or synthetic fluoride minerals, fluoride glass such as fluoroaluminosilicate glass, simple and complex inorganic fluoride salts, simple and complex organic fluoride salts or combinations thereof. Optionally, these fluoride sources can be treated with surface treatment agents.

The glass ionomers, as an example of fluoride-releasing material, can be rather brittle materials with a high modulus of elasticity, low diametral tensile strength and low fracture toughness. They can be susceptible to desiccationand, and hence can be protected with a varnish or a resin bonding agent during the setting process.

Glass ionomer materials exhibit a sustained release of fluoride over a long period of time. The uptake of the released fluoride ion in human saliva, and its incorporation into human enamel, have been reported. Studies have shown that glass ionomers inhibit demineralization of the surrounding tooth structures in vitro and in situ, and provide protection against recurrent caries under clinical conditions for patients with high caries risk. This can be attributed to the ability of glass ionomer cements to inhibit demineralization and enhance remineralization through release of fluoride to the adjacent tissue and surrounding fluid.

Filler material for incorporation in compositions of the second material or caries inhibiting material can include all those known in the art of effecting high impact strength, resistance to moisture invasion, etc., such as exhibited by inorganic silicates as well as other fillers known in the art. These silicates include amorphous silica, glass, quartz, and alumina. In particular, silica and silane-treated silica have been found to be especially useful with the interpolymers described herein.

Other ingredients can be included as necessary to achieve particularly good results. For example, it has been discovered that the use of methacrylic acid is especially effective to attain a secure deposition. It is believed that the methacrylic acid acts as a wetting/etching agent in that it alters slightly the surface of the crown, i.e., "roughens" the surface, so that the liquid reactants will readily adhere thereto, while at the same time the methacrylic acid makes the liquid reaction mixture more compatible with the crown surface so that the mixture readily spreads or "wets" to such surface with ease.

Dental resins that work as a matrix for caries inhibiting material can be acrylic materials based on an ester of acrylic or methacrylic acid, typical monomers being methyl methacrylate or a diacrylate of 2,2-bis(p-hydroxyphenyl)-propane, known as BIS-(GMA) resins. The dental resin can be used as a monomer or as a monomer/polymer mixture, i.e., an incompletely polymerized resin and polymerization is completed outside of the mouth when the resin has been placed in position on the precursor crown. All such resins are available as monomers or monomer/polymer mixtures and include any necessary catalyst etc. so that, after the resin has been put in its final position, completion of polymerization occurs within a few minutes under ambient conditions.

Acrylic materials or resins can be utilized, at least in part, as a matrix for fillers as a caries inhibiting material. Suitable acrylics or resins for use in the present invention can include methacrylate based resins, dimethacrylate based resins, hydrophobic resins, hydrophilic resins, hardenable monomers suitable for dental applications, methyl methacrylate, ethyl methacrylate, isopropyl methacrylate, butyl methacrylate, capryl methacrylate, palmityl methacrylate, stearyl methacrylate, lauryl methacrylate, Bis-Glycidyl methacrylate (Bis-GMA) based resins, 2-hydroxyethyl methacrylate (HEMA) based resins, 1,3-butyleneglycoldimethacrylate (BGD). 2,2-Bis[4-methacroyloxyphenyl]propane (Bis-MA); (Bis-GMA); 2,2-Bis[4-(2-methacroyloxy-ethoxy)phenyl] propane (Bis-EMA); 2,2-Bis[4-(3-methacroyloxy-propoxy) phenyl]propane (Bis-PMA); the dimethacrylate derivative of 1,2-cyclohexanedicarboxylic acid (c-HaDMA), the dimethacrylatederivative of 4-cyclohexene-1,2-dicarboxylic acid (c-HeDMA); and dimethacrylate monomers containing urethane groups such as UEDMA and TUDMA.

Other acrylic monomers can include, but are not limited to, ethylene glycol dimethacrylate (EGDMA), trimethylpropanetrimethacrylate (TMPTMA), polyethyleneglycoldimethyacrylate (poly-EGDMA), urethane dimethacrylates (UEDMA or UDMA) and triethyleneglycoldimethacrylate (TEGDMA) based resins.

Creating the Buccal Contour First, and then Filling the Open Space.

As described above, the method of making the dental crown 5 with the second material 7 in the open spaces 9 and/or 10, such as a caries inhibiting material to form a crown with caries inhibiting capabilities, can include steps in a specific sequence. The precursor crown 5' has an open space 9 and/or 10 in the mesial and/or distal area or mesial and/or distal side walls 11 and/or 12, in which a substantial amount of second material or caries inhibiting material, as a form of bulk or mass, is applied.

As discussed above, caries inhibiting direct restorative materials, such as in the form of composites, are very week (usually 10-50 Mpa flexural strength) It is desirable for crowns to have a flexural strength of over 120 Mpa, over 200 Mpa, over 400 Mpa, over 800 Mpa, and over 1,000 Mpa. Caries inhibiting restorative materials that can release ions and fill a ground area of a human tooth can have a resin matrix filled with fillers of caries inhibiting agents including, but not limited to, fluoride ion, calcium ion, phosphate ion, ion, zinc ion, copper ion, titania ion. The resin matrix, however, cannot withstand high temperature heat treatment required to make a strong dental crown. The resin would easily melt away over 100° C., and the crown firing or glazing temperature is at least over 500° C., and preferably over at least 800° C.

The method can comprise the sequential steps of, 1) making a precursor crown outside of the mouth with at least one of the first materials, creating the buccal contour to be generally the same as that of the final crown, wherein the precursor crown has at least one substantial open space 9 and/or 10 and open space perimeter 30 on or around at least one of the mesial 11 and/or distal 12 areas; and then, only after step one mentioned above, 2) applying a second material 7 or a caries inhibiting material, different from the first restorative material 6, inside the open space of the precursor crown while outside the patient's mouth.

The reasons why combining caries inhibiting material and dental crowns is technically very challenging is explained in detail below.

There are generally two methods of the crown making process depending on the material used. The first method is the one that produces a strong substructure first and then a top portion of supra-structure. Substructures are usually made of metal or strong ceramic material. The supra-structure is built up on this substructure using porcelain powder made of inorganic materials like $Al_2O_3$, $SiO_2$, $K_2O_3$, CaO, etc. After the supra-structure has the build-up finished on top, the whole crown is treated with a high temperature firing process (normally over 500° C.) for desirable strength, and further glazing process (normally over 800° C.) for glazed or polished effect. Crowns with a metal substructure are called PFM (porcelain fused to metal), and for zirconia substructure are called PFZ (porcelain fused to zirconia). For example, see PTC Textbook Series (PTC Dental, CA, USA) "Anterior and Posterior Porcelain Application". The second method utilizes CAD (computer aided design)/CAM (computer aided manufacturing) processing to mill a block of material to achieve a full shape crown that does not need a supra-structure material. In this method, the overall tooth shape, including the buccal contour is designed with computer software, and the whole crown is milled with a milling machine.

According to all dental technicians and all dental crown making processes, by the time the buccal contour is formed, hardened and created substantially or exactly to be that of the final crown, the mesial and/or distal area also should have already been formed to create the same mesial and/or distal contour that is substantially or exactly formed to be that of the final crown. One of the most important areas of the dental crown is the buccal contour, or labial contour in the case of an anterior crown, since it is very easily noticeable when smiling. The fact that the buccal contour has been formed, hardened and created substantially or exactly to be that of the final crown means that the crown making process is substantially done. As shown in FIGS. 6a-7c and 12e-12h, the buccal contour 14 can be finished before or after the creation of open space 9 and/or 10 The buccal contour 14 can either be finished before, or after, or even during the formation of the open space.

The buccal contour can be finished first, however, before filling the open space 9 and/or 10 with the second material. The reason that shaping the buccal contour 14 of the crown can be finished before filling the open space on or around the mesial and/or distal area with the second material of caries inhibition includes that this can be the most efficient way of attaining the aesthetics required of the crown. The buccal side of the crown is very easily noticeable to other people so it preferably needs to be aesthetically finished before the second material of caries inhibition is applied into a mesial and/or distal open space. If the buccal (and mesial and/or distal areas) does (do) not have the same contour as that of the final crown, and remains generally open to require more application (veneering or build up) of the second material of caries inhibition composite material, or other type of composite or ceramic material, or porcelain ceramic material that mandates high temperature heat treatment, then making an aesthetically acceptable crown may be virtually impossible or extremely inefficient due to the strength issues of the materials and high temperature heat treatment issues, and would take too much time for final contouring of the buccal area of the crown. In addition, another reason that shaping the buccal contour can be finished before filling the open space includes that there may not be any practical benefit in applying a caries inhibition material on the buccal side of crown because the ions of caries inhibiting materials can easily be washed away by intraoral fluids like saliva before the ions can reach the adjacent natural teeth. Test results show that the fluoride ion is incorporated into the hydroxyapatite crystals of the enamel and dentin, over an area of approximately 1-3 mm surrounding the restoration, forming hydroxyfluorapatite.

Amount of Caries Inhibiting Material

It is believed that a superior efficacy in caries inhibition to have mass or bulk form of the second caries inhibiting material applied on the sides of the precursor crown 5' than a thin deposit of the same material. Thus, it is believed that the ability of a fluoride containing restorative material in bulk or mass form to sustain fluoride release over a long period of time, rather than an ability to demonstrate a high "burst" of fluoride release immediately following placement. Such is a consequence of the nature of the carious process; carious tooth destruction develops as demineralization exceeds re-mineralization over months to years rather than at a single point in time.

the Sequential Steps of the Current Inventive Processing

As described above, the method can comprise a specific sequence of making the crown. First, the dental lab can receive the margin line 17 information of a prepared tooth 2 so that the crown margin line 18 and prepared tooth margin line 17 correspond with each other at a later stage.

Then, a precursor crown 5' can be made, outside of the mouth, with at least one of the first materials 6, creating the buccal contour to be generally the same as the final crown, wherein the precursor crown 5' has at least one substantial open space 9 and/or 10 and open space perimeter 30 on or around at least one of the mesial 11 and/or distal 12 areas, or mesial and/or distal side walls. To be more specific, the steps mentioned above could be further to make a precursor crown 5' outside of a mouth with at least one of the first restorative materials 6, wherein the buccal contour of the hardened precursor crown is the same as, or substantially the same as, or proportionately larger than that of, the final crown 5, wherein a majority of the portion of the buccal surface of the precursor crown becomes the buccal surface of the final crown before polishing and/or glazing, wherein the precursor crown 5' has at least one substantial open space 9 and/or 10 and open space perimeter 30 on or around at least one of the mesial 11 and/or distal 12 areas (or mesial and/or distal side walls), wherein the margin line 18 of the crown generally, or proportionately, corresponds the margin line 17 of the prepared tooth.

"Hardened" in the explanation of a hardened precursor crown can mean any one of the following conditions; 1) pre-sintered to be not fully sintered and as a result easily millable for a zirconia crown, 2) finally sintered and having full strength as a zirconia crown, 3) surface is baked/fired with the porcelain oven for a porcelain crown—just a lump of porcelain powder mixed with liquid before the baking/firing is not a hardened condition, 4) millable surface of any CAD/CAM milling blocks/blanks, 5) cured surface of any (resin) composite material, 6) cured surface of any 3D printed material.

Figure 12E:
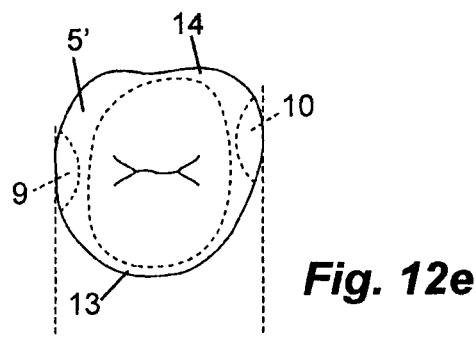
FIGS. 12e, 12f, 12g and 12h are top views of the precursor crown before filling the pockets or open spaces with a second material or a second caries inhibiting material; and with FIG. 12e showing a buccal contour the same as the final crown.
Figure 12F:
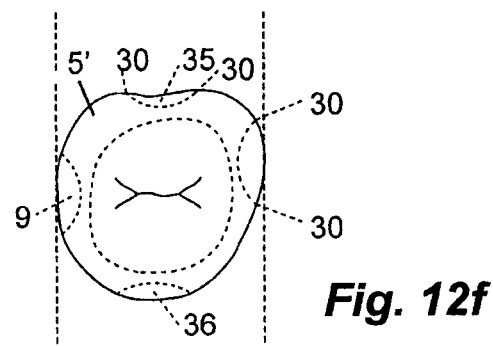
Figure 12G:
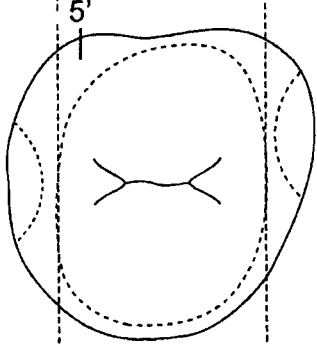
Figure 12H:
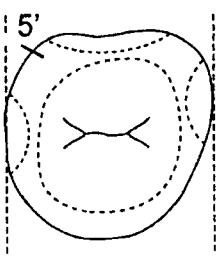
Figure 12Q:
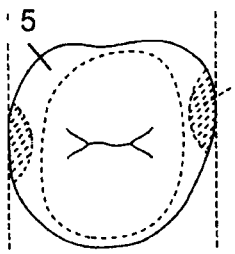
FIG. 12q is an occlusal view of the final crown.
Figure 12I:
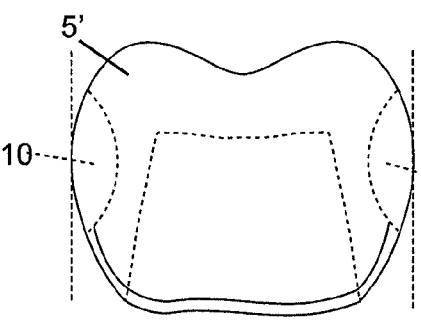
FIGS. 12i, 12j, 12k and 12l are buccal, mesial, bottom and mesial views, respectively, of the precursor crown before filling pockets or open spaces with the second material or the second caries inhibiting material.
Figure 12J:
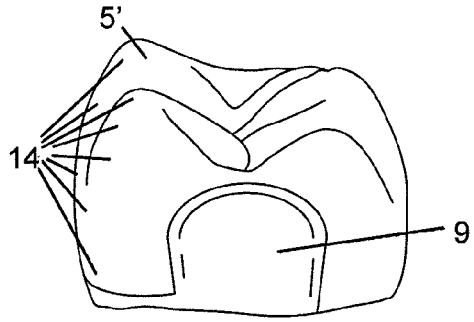
Figure 12K:
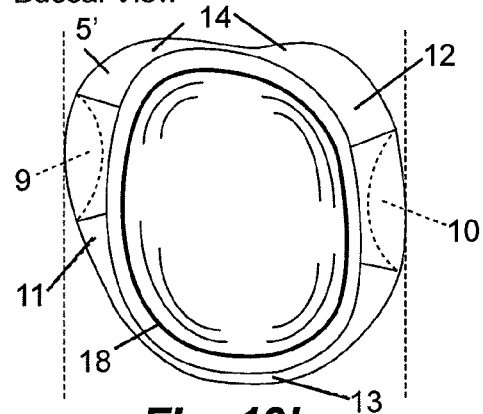
Figure 12L:
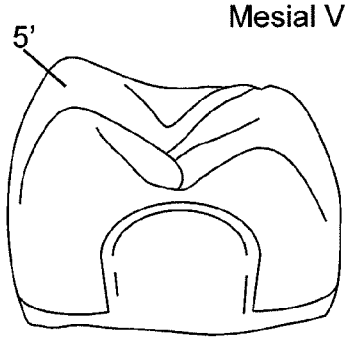
Figure 12M:
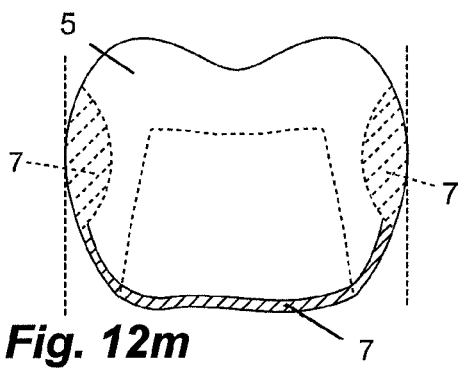
FIGS. 12m, 12n, 12o and 12p are buccal, mesial, bottom and mesial views, respectively, of the crown after filling the pockets or open spaces with the second material or the second caries inhibiting material.
Figure 12N:
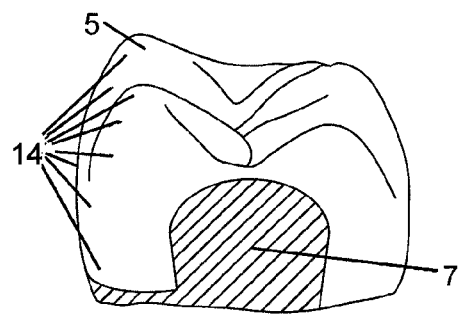
Figure 12O:
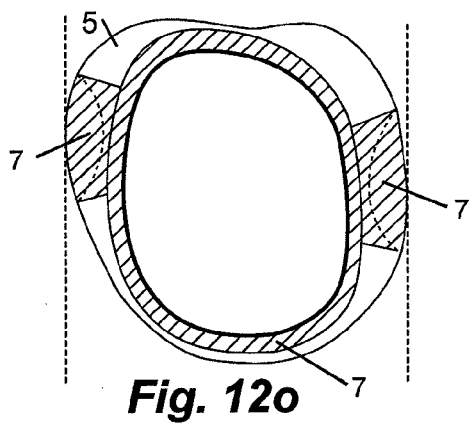
Figure 12P:
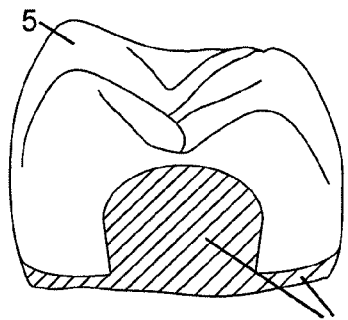
Figure 14A:
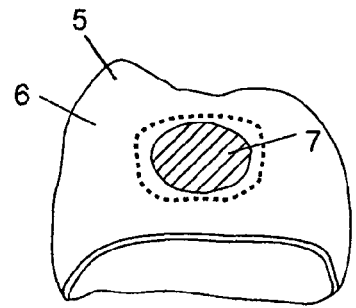
FIGS. 14a, 14b, 14c and 14d are mesial side views of the final crown with different locations and sizes of open space after being filled with the second material or second caries inhibiting material with respect to a contact area with an adjacent tooth; with an adjacent tooth; with FIG. 14a showing a contact area surrounding or circumscribing the pocket or open space (i.e. with an open space perimeter inside a contact area perimeter)

Having substantially the same buccal contour as that of the final crown 5 would mean, as in FIG. 12f, for example, the open space can be located, optionally but in an aesthetically inferior way, on the buccal side of crown. Having a proportionately larger buccal contour than that of the final crown 5, as in FIG. 12g, would apply in zirconia crown cases. Pre-sintered zirconia is milled in a larger dimension by an enlargement factor, 125 percent larger than the final size for example. If a pre-sintered zirconia blank is used to make a precursor crown 5', the buccal contour needs to be proportionately larger, for example 125 percent larger, than that of the final crown.

The high temperature heat treatment is finished by this time at any step during the above mentioned steps, and the fact that the buccal contour of the hardened precursor crown is generally the same as that of the final crown, as in FIGS. 6b, 12e, 12f, 12g, 12h and 12j, means that the crown making is substantially finished except for the open space 9 and/or 10 area. With the conventional crown making process, by the time the buccal contour is finished, the mesial and distal contour also surely must have finished, leaving no intentional open space on or around the mesial and distal area of a crown.

By this time the precursor crown is acquired in the following manner: the precursor crown can have an open contact relationship 20, as in FIG. 6a, with regards to the adjacent teeth 8, and has a strength substantially equivalent to the final crown.

The next step is to fill a second material 7 or caries inhibiting material, different from the first restorative material 6, generally inside the substantial open space 9 and/or 10 defined by the open space perimeter 30 of the precursor crown 5' while outside the patient's mouth, wherein the majority of the portion of the buccal surface of the precursor crown before filling the open space is generally the same as that of the buccal surface of the final crown before polishing and/or glazing, and wherein said second material 7 is applied on or around at least one of the mesial and the distal sides of the crown, either directly contacting the mesial and/or distal side of the adjacent human tooth 8, or being closely located to face the mesial and/or distal side of adjacent human tooth 8.

Thus, the second material 7 is disposed inside the pocket or open area 9 and/or 10 that is different from the first material 6 used for the creation of the buccal contour, specifically after the buccal contour is finished. The same material can be used for the mesial, buccal and distal contours at the same time for a long, continuous open area. In one aspect, the buccal area can be layered/veneered on the substructure, and porcelain powder can be applied on this buccal area on a metal or opaque ceramic substructure. In another aspect, different materials can be used between the mesial/distal and buccal areas or walls without a creating pocket or open area on or around the mesial and/or distal area. For example, a so-called ¾ metal crown can be made, in which the occlusal, lingual, mesial and distal areas or walls are all metal, and finished first, and then porcelain powder is applied later onto the buccal area for aesthetic purposes. Thus, the precursor crown can comprise two different first materials, such as metal and ceramic. After the buccal contour is finished, then a different second material, different than the first materials (or metal and ceramic), is disposed inside an open space or a pocket created on or around the mesial and/or distal area.

The next step is to secure the second material 7 or caries inhibiting material inside the open space or pocket while outside the patient's mouth in such a way that the second material does not get separated from the first material, or precursor crown. Securing the second material can include self-curing, heat curing, or light curing, etc. for this mostly composite material.

The surface after the application of this second material may be a bit rough. So it may be desirable to complete the contour of the final crown for the mesial and/or distal side by adjusting the surface of the second material, thereby acquiring a crown 5 having a closed contact relationship 21 with regards to the adjacent tooth 8.

The final crown has five walls of occlusal 15, mesial side 11, buccal 14, distal side 12, and lingual 13 walls. The five walls are connected to form a concavity 16 therein. The concavity 16 is contacting or receiving a prepared tooth 2 cut by a dentist, or an implant abutment 2'. Thus, the final crown 5 has a caries inhibiting material therein.

Creating an Open Space Either from an Open Contact Relationship or Closed Contact Relationship FIGS. 5 and 6a show one way of making the crown 5 in which a precursor crown 5' is made with, or that would have, a closed contact relationship 21 from the beginning to touch the adjacent teeth 8, and then the open space 9 and/or 10 can be made either manually or using a milling machine to create an open contact relationship 20 with the adjacent teeth 8.

Figures 20A, 20B, 20C, 20D, 21A, 21B, 21C, 21D:
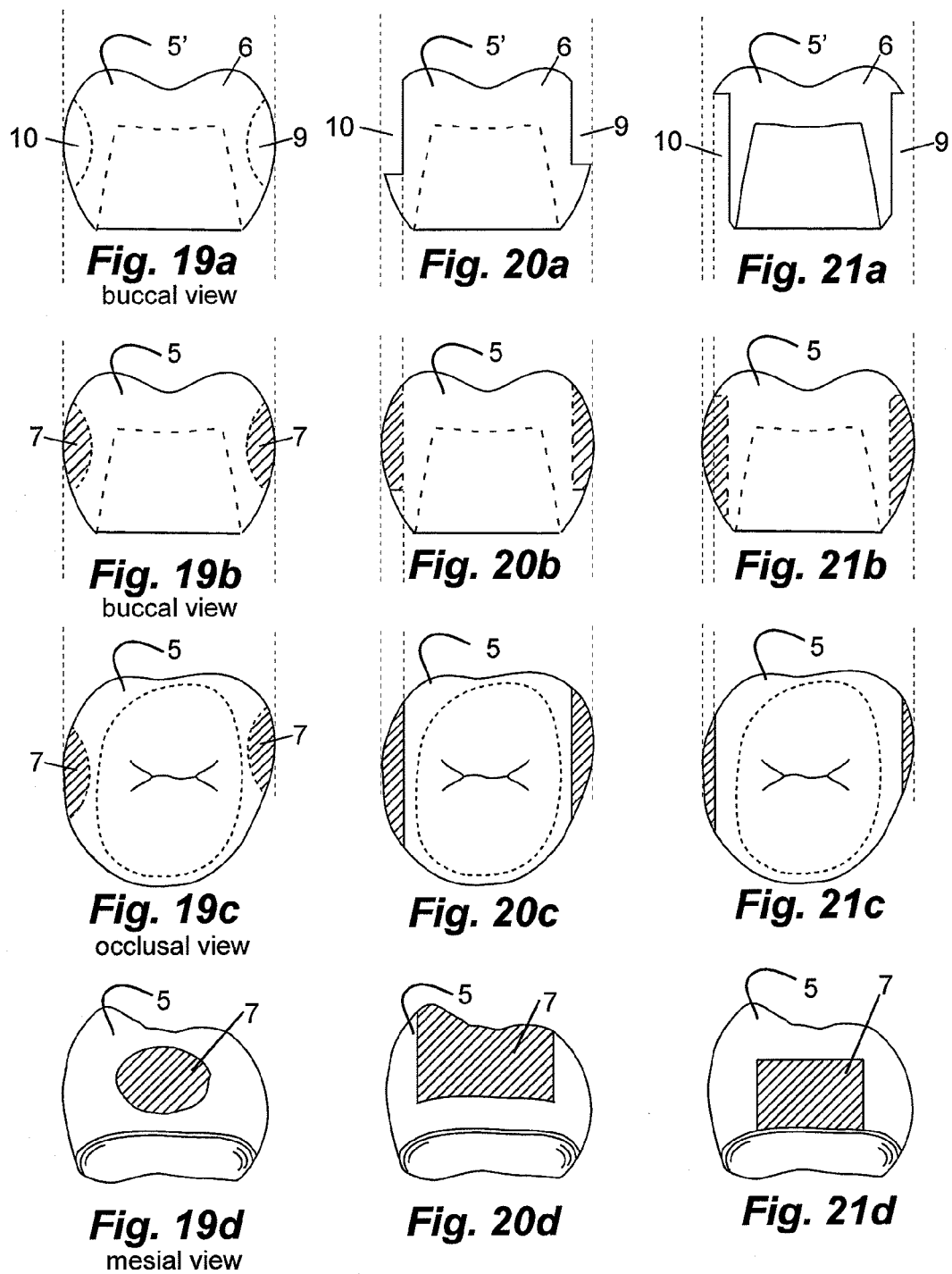

The open contact 22 noted as C in FIG. 8 can, but not always, be created by a milling machine from the CAD/CAM digital dentistry application. FIG. 8 shows another way of creating an open space 9 and/or 10 which is ground away from the open contact relationship 22 with a distance noted as C. The precursor crown 5' can be made in a way as not to touch the adjacent teeth 8, and then the mesial open space 9 on or around the mesial wall 11, and the distal open space 10 on or around the distal wall 12, is further ground down to create a space to receive a second material 7 or caries inhibiting material therein. Alternatively, as shown in FIGS. 20a and 21a, CAD (computer-aided-design) software can design the precursor crown in such a way as to create an open contact 22 relationship away from the adjacent teeth 8. At a following stage, the second material 7 or caries inhibiting material can fill the open space 9 and/or 10 to create a closed contact 21 relationship.

Contact Point and Contact Area

FIGS. 6a, 7a, 13a-d, 14a-d, 15a-c and 16a-c show a contact area 24 and a contact point 23 which are an area or point created between the crown 5 and the adjacent-and-touching teeth 8. In one aspect, a contact point can exist between a molar and bicuspid, and a contact area can exist between molars, as shown here in FIG. 6a. Contact area 24 can vary in its size from as little as a point 23, or as broad as, for example, 1 cm² or more in its dimension. Contact area 24 and/or point 23 can be important in oral health, form and function. When an indirect restoration is made without a contact area, food debris can easily become stuck between the teeth, or teeth can slowly shift towards the open contact area over a long period of time, resulting in a structural malfunction of the overall teeth.

Location of the Open Space in Relation to the Contact Area

Figure 13A:
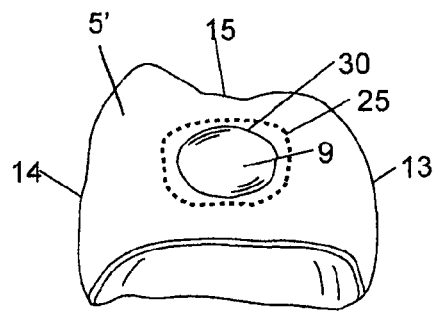
FIGS. 13a, 13b, 13c and 13d are mesial side views of the precursor crown with different locations and sizes of pockets or open spaces before being filled with the second material or second caries inhibiting material with respect to a contact area with an adjacent tooth; with FIG. 13a showing a contact area surrounding or circumscribing the pocket or open space (i.e. with an open space perimeter inside a contact area perimeter)
Figure 13B:
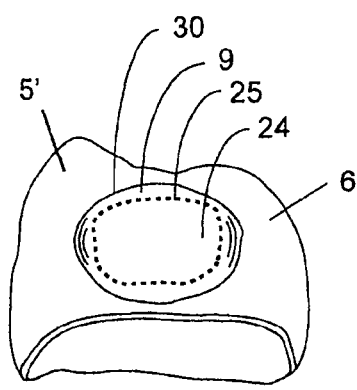
Figure 14B:
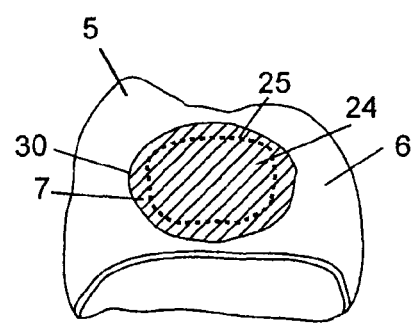
Figure 13C:
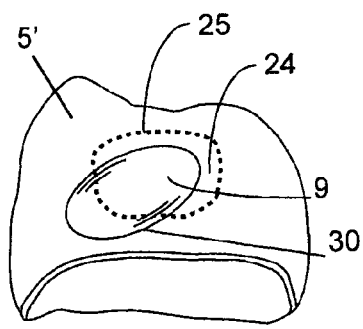
Figure 14C:
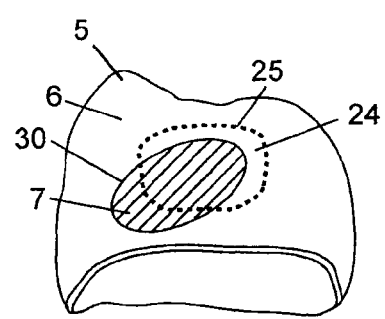

In the case of a broad contact area 24, as shown in FIGS. 13a, 13b, 13c, and 13d, the open space 9 and/or 10 that is created on or around at least one of the mesial and distal contact areas generally may exist as four types. First, as in FIG. 13a, the open space 9, defined by open space perimeter 30, can exist inside the contact area perimeter 25. In this case, the open space 9 that receives a caries inhibiting material 7 is rather small, but directly releases the fluoride ion (F⁻), for example, towards the abutting natural teeth. Secondly, as shown in FIG. 13b, the open space 9, defined by open space perimeter 30, can completely encompass the contact area 24 defined by contact area perimeter 25. In this case, the patient can get a benefit from the increased effect of a caries inhibiting material, but the crown may have a slightly mismatched aesthetic look between the first material 6 of the body material and the second material of caries inhibiting material. Thirdly, as in FIG. 13c, the open space 9 may exist partially inside and, at the same time, partially outside the contact area 24 defined by contact area perimeter 25. Fourthly, as in FIG. 13d, the open space 9 can exist completely outside of the contact area 4 defined by contact area perimeter 25, but still near the contact area 24 so that the adjacent teeth can get a benefit from the released fluoride ion (F⁻) effect. The number of open spaces 9 can be one or multiple as needed. FIGS. 14a, 14b, 14c and 14d show the caries inhibiting material filling each of the open spaces 9 corresponding to FIGS. 13a, 13b, 13c and 13d. By applying the caries inhibiting material, the precursor crown 5' restoration now generally closes the open contact gap 20 (noted as A in FIG. 6a) and generally creates a closed contact relationship 21 (noted as B) as shown in FIG. 7a.

the Relationship Between the Open Space and Open Contact

Figure 13D:
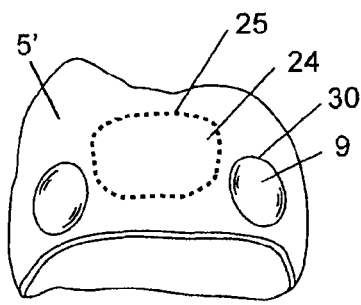
Figure 14D:
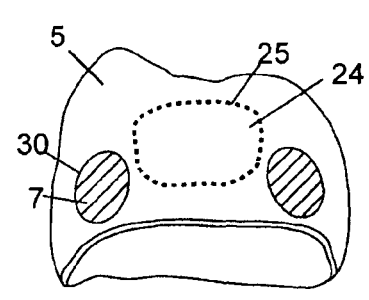

As shown in FIG. 6a, open space 9 and/or 10 created on the precursor crown 5' generally creates an open contact 20 relationship. If open space 9 and/or 10 is created outside of the contact area perimeter 25, as shown in FIG. 13d, it creates a closed contact relationship though. In other words, open space 9 and/or 10 of precursor crown 5' can create an open contact relationship, but in some cases it could still create a closed contact relationship.

For specific example, as in FIG. 7a, a full contour zirconia crown 5 can be first CAD (computer aided design) designed so that the mesial 11 and distal 12 area can abut with the adjacent teeth 8, creating a closed contact relationship 21. Creating a closed contact generally means a restoration without an open space. An exception of this, as shown in FIG. 13d, would be a case where an open space 9 would exist outside the contact area 25. In other words, a precursor crown 5' can have a closed contact and still have at least one open space 9.

Contact Point and Open Space

Figure 15A:
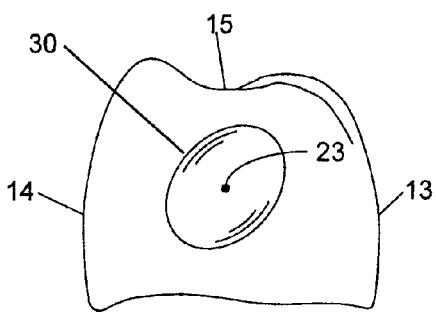
FIGS. 15a, 15b and 15c are mesial side views of the precursor crown with different locations and sizes of open spaces before being filled with the second material or second caries inhibiting material with respect to a contact point with an adjacent tooth; with FIG. 15a showing a contact point within an open space perimeter.
Figure 16A:
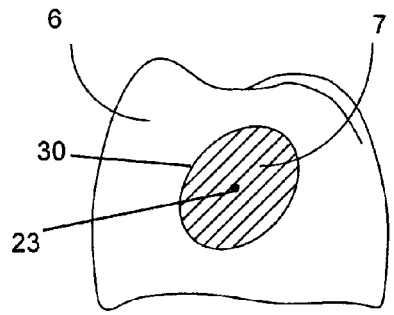
FIGS. 16a, 16b and 16c are mesial side views of the final crown with different locations and sizes of open space after being filled with the second material or second caries inhibiting material with respect to a contact point with an adjacent tooth; with FIG. 16a showing a contact point within an open space perimeter.
Figure 15B:
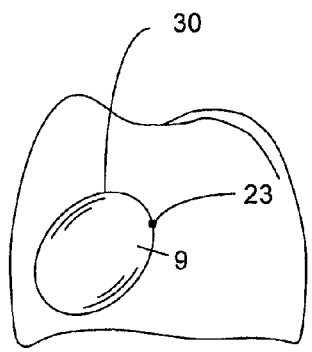
Figure 16B:
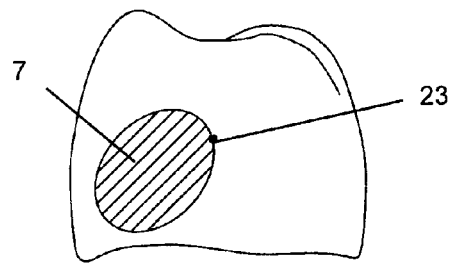
Figure 15C:
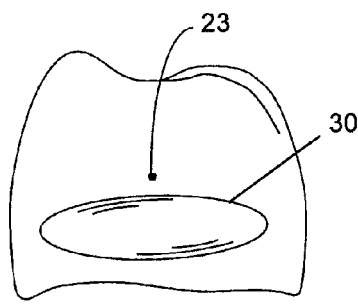
Figure 16C:
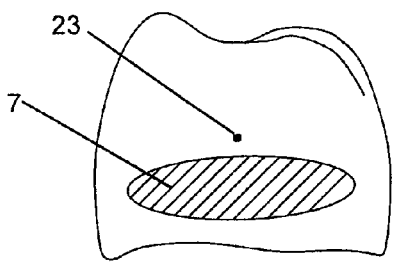

FIGS. 15 and 16 show that the contact area of a crown can be small enough to be practically a point 23. Similarly, the open space 9 defined by the open space perimeter 30 can encompass the contact point as in FIG. 15a, or the open space perimeter 30 may exist on the contact point 23 as in FIG. 15b. Or the open space 9 can exist completely outside of the contact point 23, but still near the contact point 23 so that the adjacent teeth can get a benefit from the caries inhibiting material.

Anterior Crown and the Open Space

Figure 17A:
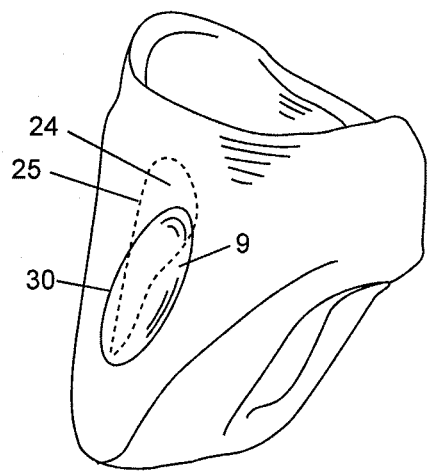
FIGS. 17a and 17b are mesial side views of a precursor crown with different locations and sizes of open spaces before being filled with the second material or second caries inhibiting material with respect to a contact area with an adjacent tooth.
Figure 17B:
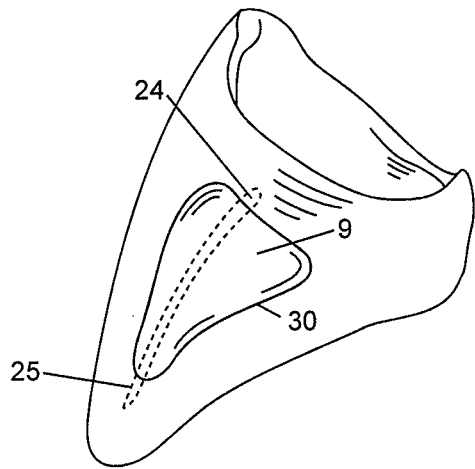
Figure 18A:
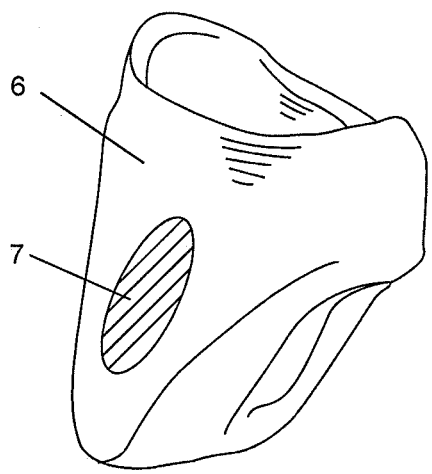
FIGS. 18a and 18b are mesial side views of a final crown with different locations and sizes of open space after being filled with the second material or second caries inhibiting material with respect to a contact area with an adjacent tooth.
Figure 18B:
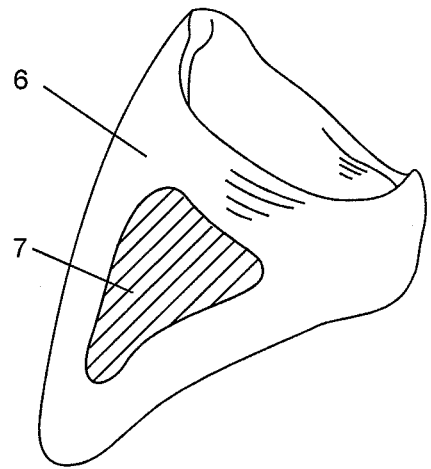

FIGS. 17a and 17b show an alternative aspect of the crown. The contact area 24 is either a narrow area in FIG. 17a, or almost a line in FIG. 17b between the two immediately abutting anterior teeth. The open space 9 can also be placed either on, or along, or covering, or near the (broad or thin) linear contact area 24 as in FIG. 17a. FIG. 17b shows a thin linear contact area.

Different Shapes of the Open Space

FIGS. 19, 20 and 21 show different aspects of form and shape of the open space 9 and/or 10, and how it can be created from various directions, with different sizes and modes. As shown in FIG. 19a, an open space 9 and/or 10 can be created, such as manually, from both mesial and distal directions using an undercut area. The shape of the undercut can preferably be a concave form. FIG. 20b shows an indirect crown restoration with an open space created from the top direction, typically by a milling machine. Caries inhibiting material fills this undercut area of a precursor crown 5' to create a smooth and continuous contour perfecting the natural tooth shape and ultimately becoming a final crown 5. FIG. 21a shows a precursor crown 5' with an open space created from the bottom direction, typically by a milling machine. FIGS. 19d, 20d and 21d show a mesial or distal aspect of the crown 5 corresponding to precursor crowns in FIGS. 19a, 20a and 21a.

Precursor Crown Having the Same or Substantially the Same or Proportionately the Same Buccal Contour as that of the Final Crown FIGS. 10a-d, 11a-d and 12a-d show another aspect of the precursor crown 5' having the same or substantially the same buccal contour as the final crown 5, and having at least one extra open space other than the open space on the mesial 11 and distal 12 areas. Providing an open space 35 on the buccal 14 area and filling this space 35 with caries inhibiting material may detract from the aesthetic aspect of the final crown 5. Also, caries inhibiting material provided on the lingual 13 open space 36 may have a high possibility of being washed away easily by the intraoral fluid, like saliva. Still, providing the functional second material like caries inhibiting material anywhere on the crown may better than not providing it at all. As in FIG. 11a, the area between mesial 11 and buccal 14 is called mesio-buccal, and the area between mesial 11 and lingual 13 is called mesio-lingual. For the same manner, the area between distal 12 and buccal 14 is called disto-buccal 42, and the area between distal 12 and lingual 13 is called disto-lingual. Open spaces can be provided on at least one of the mesio-buccal 40, mesio-lingual 41, disto-buccal 42, and disto-lingual 43 areas. The mesio-buccal area 40 and mesio-lingual area 41 is considered as part of the mesial area. The disto-buccal area 42 and disto-lingual area 43 is considered to be a part of distal area. As shown in FIG. 12a, the precursor crowns that has a buccal open space 35 or lingual open space 36 are still regarded as a precursor crown that has substantially the same contour as the final crown since the open space 35 or 36 on the buccal 14 or lingual 13 area is considered to be relatively small compared to the final crown dimension. It is believed that the most effective area for the carried inhibiting material is the mesial and/or distal area of a crown. Any variation of the location would be possible for a person having ordinary skill in the art, as in FIG. 12a.

Figure 22:
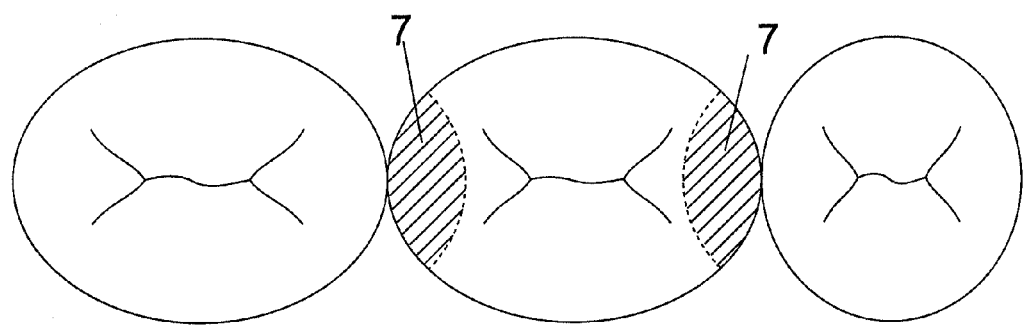
FIG. 22 is a top or occlusal view of the final crown with respect to adjacent teeth and showing the contact area is closed with the second material or the caries inhibiting material.
Figure 23:
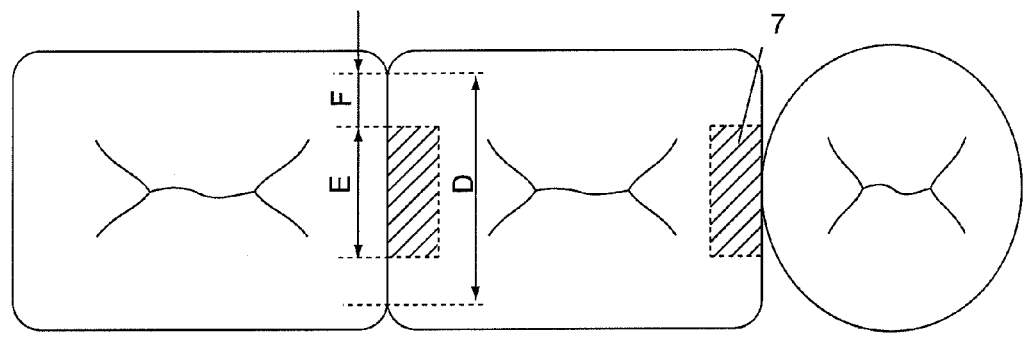
FIG. 23 is a top or occlusal view of the final crown with the pocket or open space filled with the second material or caries inhibiting material and showing a heavy contact area on the distal area of the crown and contact point on the mesial area of the crown.
Figure 24A:
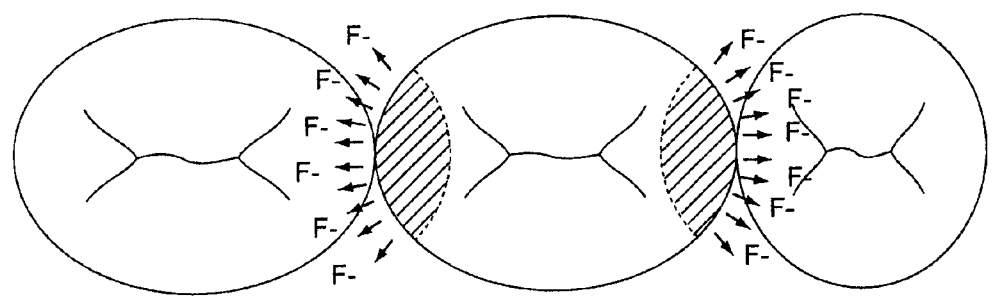
FIGS. 24a and 24b are top or occlusal views of the final crown with a second caries inhibiting material, namely fluoride, releasing restorative material as a typical example of a caries inhibition material.
Figure 24B:
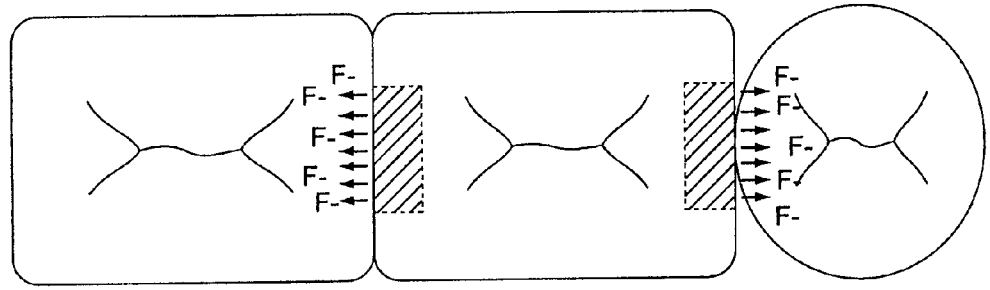

Aspects of the Open Space Filled with Fluoride Releasing Material in Relationship to the Adjacent Teeth FIG. 22 shows the contact point relationship between the immediately abutting teeth. Two teeth meet almost at one point, whereas FIG. 23 shows a broader contact area noted as D. In this case, the open area 9 and/or 10 can be as wide as E, or as wide as D. FIGS. 24a and 24b shows the fluoride ions (F−) released from the fluoride releasing material, as one of the most typical examples of caries inhibiting materials 7, filling the open area 9 and/or 10.

Bridge Restoration Cases with an Open Space on Both Sides

Figure 25:
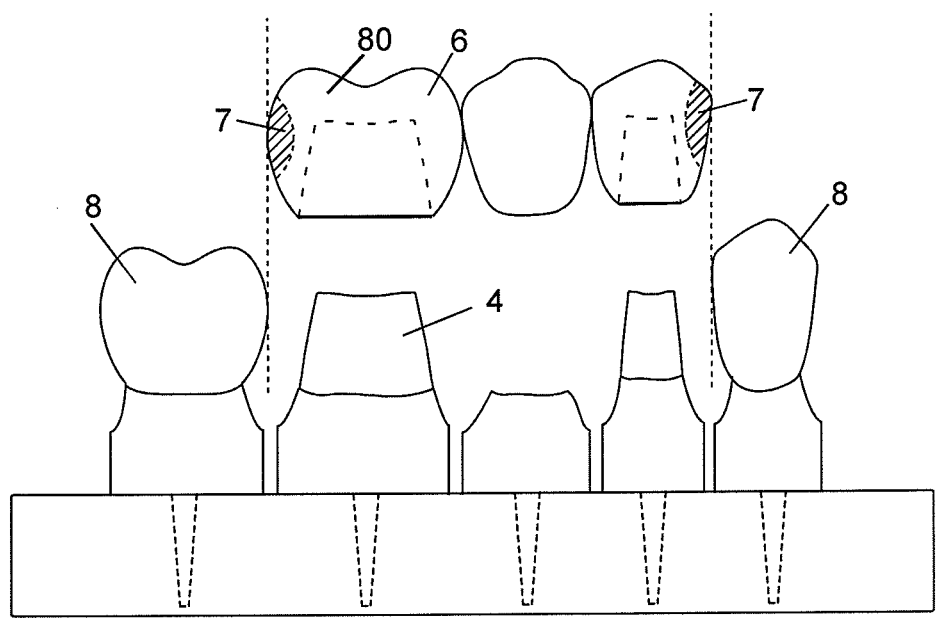
FIG. 25 is an exploded side view of a sectioned dental stone model with a dental prosthesis or restoration, namely a bridge, in accordance with an embodiment of the invention.
Figure 30A:
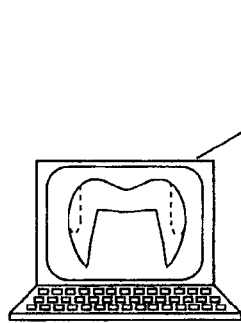
FIGS. 30a-30d are schematic view of a method and apparatus for forming a precursor crown.
Figure 30B:
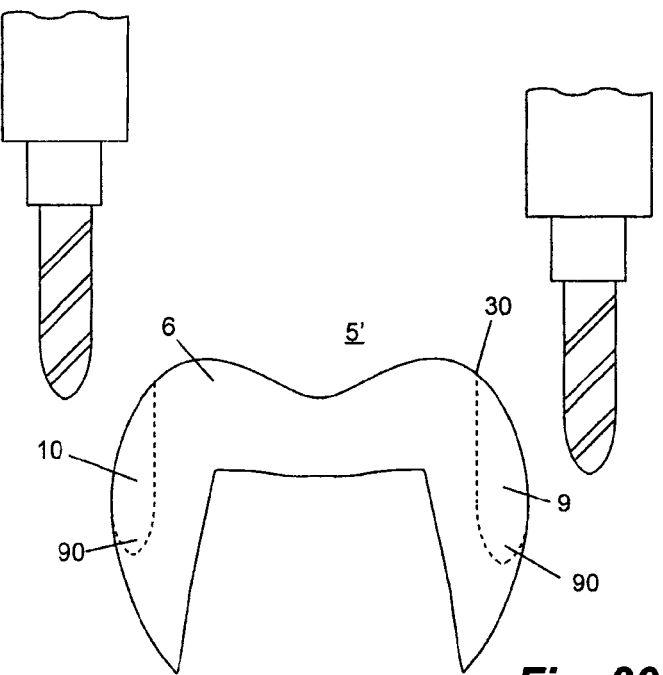
Figure 30C:
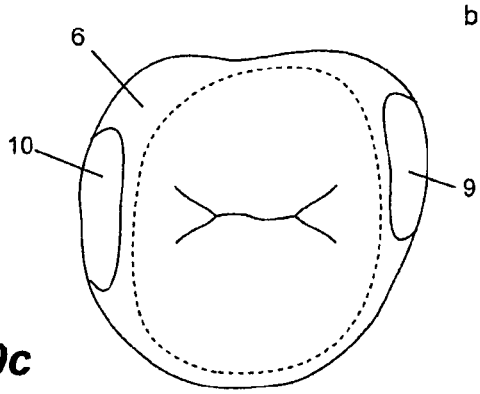
Figure 30D:
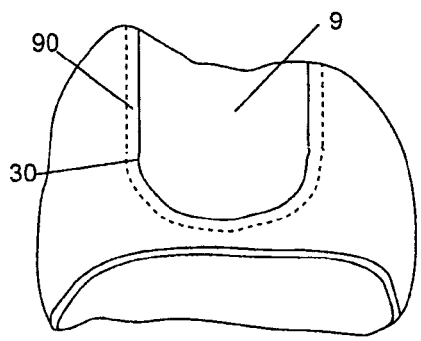

In other aspect of the current invention, the open area 9 and/or 10 can be created in a multi-unit bridge 80 as shown in FIG. 25. In this case, there usually exists one mesial open space and one distal open space regardless of the numbers of restored teeth units.

Method of Mechanically Securing Fluoride Releasing Material Inside the Open Space FIG. 26 shows another aspect of the current invention with a mechanical lock mechanism for the second material or the caries inhibiting material inside the open space 9 and/or 10. A ball shaped carbide or diamond bur 91 can be used to create an undercut area 90 in open space 9 and/or 10. This undercut area 90 works as a locking means by which the cured second material or the caries inhibiting material, such as in the form of resin modified glass ionomer composite, is mechanically locked so as not to be dislodged over a long period of time.

Test 1—Benefit of Caries Inhibiting Fluoride Releasing Material in the Open Space Purpose An In-vitro test was done to prove that the caries inhibiting fluoride releasing material applied in the open space of a current inventive crown inhibits the de-mineralization (lesion progression) and promotes the re-mineralization (repair) of the adjacent tooth enamel.

Method

Figure 34:
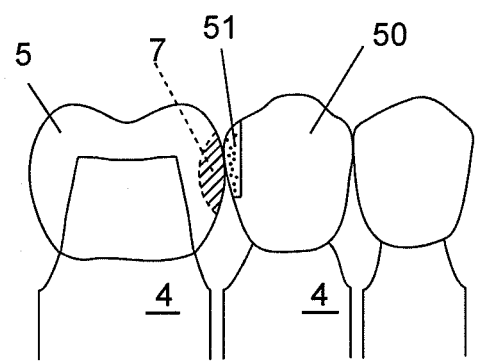
FIG. 34 is a side view of the final crown with the pocket or open space filled with the second material, namely the caries inhibiting material, and a regular crown attached with a human enamel sample, for a comparative test.
Figure 35:
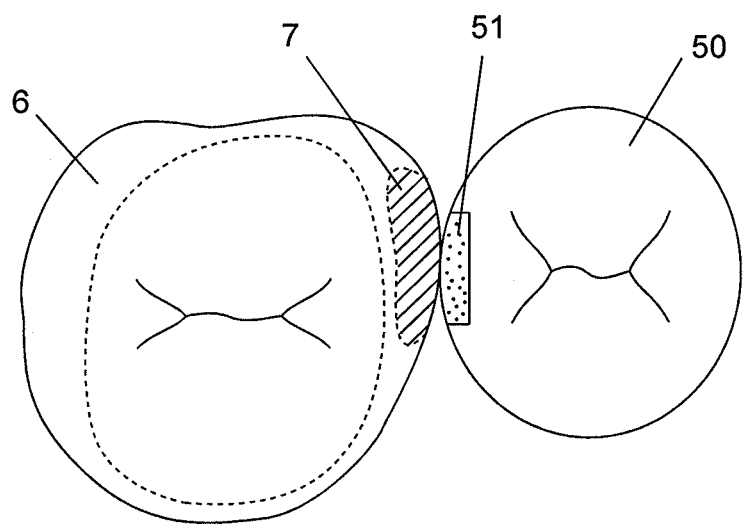
FIG. 35 is a top view of the final crown and the regular crown of FIG. 34.
Figure 38:
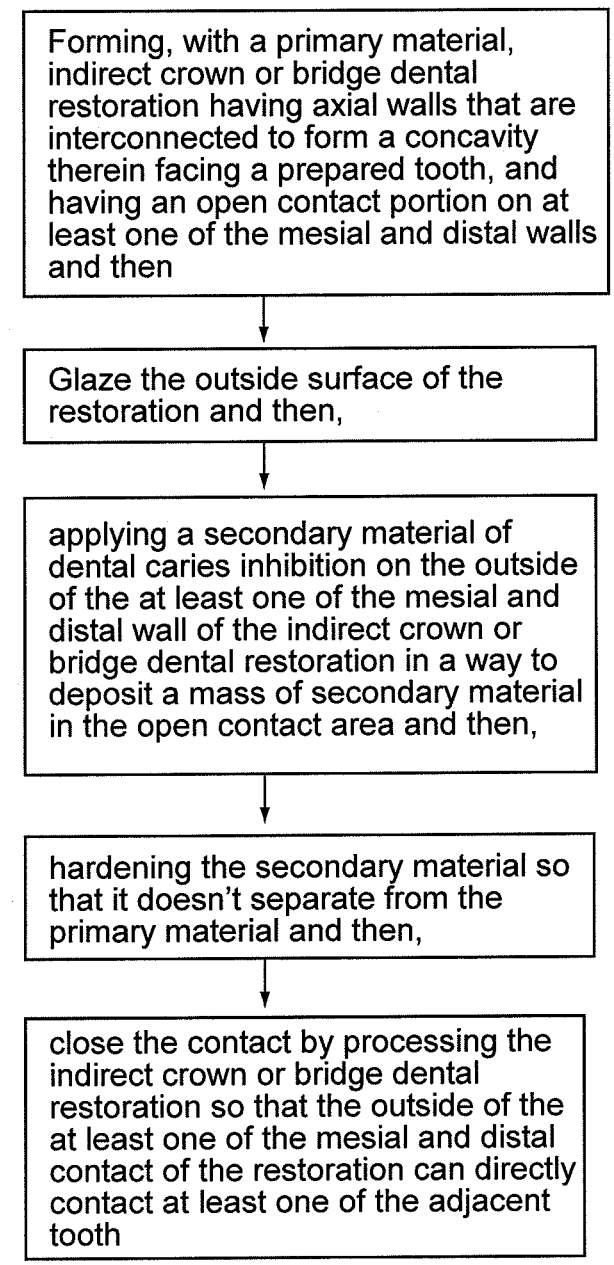
FIG. 38 is a flowchart showing a method for making a dental prosthesis or restoration, such as a crown.

Forty sets of full coverage molar crowns 5 and adjacent bicuspid crowns 50 were prepared as in FIGS. 34 and 35, and firmly seated on the dental model 4. The molar crown 5 had a mesial open space and caries inhibiting fluoride releasing restorative material 7 (Vitremer, 3M) was applied in the open space. A small piece (2 m×2 mm) of sectioned human tooth enamel 51 was placed on the distal side of adjacent bicuspid crown restoration 50. Then, artificial caries lesions were created at the external tooth enamel surface 51 and placed on the distal side of the bicuspid crown 50 for the evaluation of further demineralization, caries arrestment, or re-mineralization. The artificial caries solution contained 2.0 millimolars, or mmol/L, of calcium, 2.2 mmol/L phosphate and 50 mmol/L acetic acid at a pH of 4.4, at a temperature of 37 C; the solution constantly circulated around the bicuspid crown 51 until an artificial carious lesion was induced. It took five days to create these artificial carious lesions. The presence of such a lesion was determined visually, then confirmed by polarized light microscopy. We obtained distal 100-micrometer longitudinal sections with a Silverstone/Taylor (ScientificFabrications) microtome, placed the sections on glass slides and viewed them in an imbibition medium of water to evaluate the internal pore volume of the enamel lesions. The imbibition of water allows for detection of a pore volume of greater than 5 percent. We digitized photo-micrographs of the lesion areas represented and used these areas as baseline values for any changes resulting from the artificial saliva solution exposure. During the testing periods, the adjacent crowns 5, 51 including the die 4 were always submerged in the artificial saliva solution added with glucose solution (45% in $H_2O$) to simulate the intra oral condition. After the various phases of the study were completed, the sections 51 were carefully removed and re-evaluated in the laboratory. The same sections were then re-photographed in the water medium after completion of the treatment phases, so that changes in lesion sizes could be determined.

Preparation

This project was a four-phase study to test the de- and re-mineralization effects of 1) a glass ionomer material which naturally releases caries inhibiting fluoride (Vitremer, 3M Dental Products), and 2) a non-fluoride-releasing resin composite control material 52 (IPS Empress Direct, Enamel Light A3, IvoClar). The four experimental periods were one month each in duration. In the first experimental phase, we tested the current inventive molar crown 5 with the control material 52 (IPS Empress Direct, Enamel Light A3, IvoClar) in the open space, a non-fluoridated composite material adjacent to a bicuspid crown 51 which had tooth enamel portion 51 on the distal side that was temporarily cemented in place. Two crowns (molar 5, bicuspid 51) seated on the die 4 were then stored in the artificial saliva solution for a month. Simulated tooth brushing was done for the crowns 5, 51 seated on the die 4 twice per day for two minutes each brushing with a non-fluoridated dentifrice for the month. After each brushing, new artificial saliva solution (added with glucose solution (45% in $H_2O$)) was added so that the crowns could be submerged. At the end of the first phase, we removed the two crowns 5, 50. In the second phase, we placed another bicuspid crown 50 with enamel sections 51 and another non-fluoridated resin composite 52 in the open space in the current invention molar crown 5, as before. This time, however, we did simulated tooth brushing to brush twice daily for two minutes at each brushing using a fluoridated dentifrice (Crest, Procter & Gamble). After one month, the bicuspid crown was removed.

In the third phase, we filled the mesial open space of the current invention molar crown 5 with a caries inhibiting fluoride releasing material (Vitremer, 3M) and light cured the material so that it can directly abut with the sectioned portion of the tooth enamel 51 implanted in the distal side of the adjacent bicuspid crown 50. Then simulated tooth brushing was done for a month using non-fluoridated dentifrice twice daily. In the fourth phase, we used the same setting as the third phase but this time fluoridated dentifrice was used twice daily.

Results

The results are presented in the following Table 1.

| Phase | Number of sample sets | Caries inhibiting material in the open space of the current inventive crown | Fluoride content of dentifrice used | Average percentage change in the caries lesion area (±SD) |
|---|---|---|---|---|
| 1 | 10 | Non-fluoridated composite resin (IvoClar, IPS Empress Direct, Enamel Light A3) | 0 ppm F-(negative fluoride ion) | 20.25 ± 45.12 |
| 2 | 10 | Non-fluoridated composite resin (IvoClar, | 1,100 ppm F-(negative fluoride ion) | 0.95 ± 28.21 |

-continued

| Phase | Number of sample sets | Caries inhibiting material in the open space of the current inventive crown | Fluoride content of dentifrice used | Average percentage change in the caries lesion area (±SD) |
|---|---|---|---|---|
| 3 | 10 | IPS Empress Direct, Enamel Light A3) Fluoride releasing material- Resin modified Glass ionomer (3M, Vitremer) | 0 ppm F-(negative fluoride ion) | −10.25 ± 4.24 |
| 4 | 10 | Fluoride releasing material- Resin modified Glass ionomer (3M, Vitremer) | 1,100 ppm F-(negative fluoride ion) | −15.21 ± 21.35 |

An analysis of variance indicated statistically significant differences in variance among the experimental phases. Positive numbers for average percentage change in the caries legion area indicate an increase in demineralization, whereas negative numbers indicate re-mineralization. When crowns 5, 50 were brushed with a fluoridated dentifrice, both types of restorative materials (Non-fluoridated composite resin 52 (phase 2) and fluoride releasing material 7 (phase4)) demonstrated significantly ($P<0.05$) less enamel demineralization (0.95% and −0.15% change) than the crown with a non-fluoridated resin composite control (phase 1, average percentage change in the caries legion area was 20.25%) brushed with a non-fluoridated dentifrice. However, the current inventive crown 5 with resin-modified glass ionomer, even when brushed with a non-fluoridated dentifrice (phase3), exhibited significantly ($P<0.05$) less demineralization (−10.25%) than the non-fluoridated resin composite control material 52 brushed with a non-fluoridated dentifrice (20.25%). The current invention crown 5 (phase 4) with an open space in which a caries inhibiting resin-modified glass ionomer was applied, when brushed with a fluoridated dentifrice, not only demonstrated significantly ($P<0.05$) less demineralization (−15.21%) than the non-fluoridated resin composite control (phase1) brushed with a non-fluoridated dentifrice (20.25%), but also significantly ($P<0.05$) less demineralization than the fluoridated resin composite brushed with a non-fluoridated dentifrice (phase3, −10.25%).

The present invention will be further understood in view of the following examples, which are merely illustrative and not meant to limit the scope of the invention.

Example 1

Full Contour Zirconia, Manual Creation of the Open Space (Margin line, Design of a crown with a closed contact) Margin line information of a cut tooth was received before starting to make a crown. As in FIG. 3, the crown margin line 18 was created to cause the crown margin line 18 and prepared tooth margin line 17 to correspond with each other. A full contour zirconia crown was first CAD (computer aided design) designed so that the mesial and distal area of the crown could abut with the adjacent human teeth, creating a closed contact as introduced in option 1-1 in FIG. 6.

(Automated milling and manually creating the open space) Then this precursor crown, primarily made of $ZrO_2$, was milled from a pre-sintered zirconia block using the CAD/CAM method. Afterwards, a small undercut 9 and/or 10 on each of the non-load bearing mesial and distal areas was created by grinding away the ceramic body portion with a hand tool, creating hollow open spaces 9 and/or 10 as shown in FIG. 6a. After the completion of making the open space pit, the precursor crown 5' already had substantially the same buccal contour 14 (FIG. 6b) as that of the final crown 5 as in FIG. 7b.

(Firing, Sintering) Then a high temperature (1,400-1,550° C.) heat treatment was applied to the precursor crown in a final sintering stage to achieve desired strength.

(Glazing) Then the outside of the precursor crown 5', except the open space 9 and 10, was glazed at a temperate of 500-1,100° C. for a polished effect.

(Applying fluoride releasing material) After glazing, an etchant (ETCH-37, 37% phosphoric acid etchant with benzalkonium chloride, Bisco, USA) was applied on the open space area of the precursor crown 5' for better adherence of the fluoride releasing material to the zirconia crown. Then a caries inhibiting fluoride releasing material 7 (0.3 gram, KetacNano, 3M, Germany) was applied on each side of the non-load bearing area of the mesial and distal open space 9,10.

(Curing)) The material applied on the precursor crown 5' was then light cured for polymerization.

(Finishing the mesial and/or distal surface) After polymerization, the surface of the applied fluoride releasing material 7 was evenly adjusted by grinding with a dental hand wheel to match the contour of the rest of the final crown 5.

Example 2

Full Contour Zirconia, Automated Milling Machine Creates Open Space (Margin line, Design of a crown with an open contact) Margin line information of a cut tooth was received before starting to make a crown. The crown margin line 18 was created to cause the crown margin line 18 and prepared tooth margin line 17 to correspond with each other. A full contour zirconia crown was first CAD (computer aided design) designed so that the non-load bearing mesial and/or distal area could have an open space 9 and/or 10 away from the adjacent teeth 8, creating an open contact as introduced in option 2-1 in FIG. 6, or FIG. 20a or FIG. 21a.

(Automated milling and mechanically creating the open space) Then this precursor crown 5', primarily made of $ZrO_2$, was milled from a pre-sintered zirconia block using the CAD/CAM method. At least one open space 9 and/or 10 was milled from the milling machine. The automated milling process can create the buccal contour 14 either before, or during, or after the creation of the open space 9,10.

(Firing, Sintering) Then a high temperature (1,400-1,550° C.) heat treatment was applied to the precursor crown 5' in a final sintering stage for desired strength.

(Glazing) Then the outside of the precursor crown, except the open space, was glazed at a temperate of 500-1,100° C. for a polished effect.

(Applying caries inhibiting material) After the glazing, an etchant (ETCH-37, 37% phosphoric acid etchant with benzalkonium chloride, Bisco, USA) was applied on the open space area of the precursor crown 5' for better adherence of the fluoride releasing material 7 to the zirconia crown. Then a caries inhibiting fluoride releasing material 7 (0.3 gram, Equia, GC, Japan) was applied on each side of the non-load bearing area of mesial and distal open space 9 and/or 10.

(Curing) The material applied on the crown precursor was then photo-cured for polymerization with a LED unit with a controlled wave length of 440-480 nm for 60 seconds.

(Finishing the mesial and/or distal surface) After polymerization, the surface of the applied caries inhibiting material 7 was evenly adjusted by grinding with a dental hand wheel to match the contour of the rest of the final crown 5.

Example 3

Full Contour Zirconia, Light Curing (Design of a restoration with or without an open space) A full contour zirconia crown was first CAD (computer aided design) designed on the computer monitor as in FIG. 6 so that the mesial and distal area could abut with the adjacent teeth 8 (option 1-1), creating a closed contact. Creating a closed contact generally means a restoration without an open space. An exception of this would be a case where an open space would exist outside the contact area. In other words, a precursor crown 5' can have a closed contact and still have at least on open space as in FIG. 13*d*. Alternatively, as in FIG. 8, a full contour zirconia crown was first CAD (computer aided design) designed on the computer monitor so that the non-load bearing mesial and/or distal area can have an open space away from the adjacent teeth 8, creating an open contact 18. Alternatively, open contact of the inventive precursor crown 5' can be created through option 2-1 of FIG. 6 or FIG. 20*a* or FIG. 21*a*.

(Milling & creating the open space undercut) Then this precursor crown 5' primarily made of $ZrO_2$ was milled from a pre-sintered zirconia disk using the CAD/CAM method. Afterwards, an undercut on each of the non-load bearing mesial and distal areas was created by grinding away the ceramic body portion with a hand tool, creating hollow open spaces 9 and/or 10 as shown in FIG. 6*b*. Alternatively, if the precursor crown was CAD designed with an open space, then at least one open space can be milled from the milling machine. After the completion of making the open space pit, the precursor crown has already had the same or substantially same buccal contour as that of the final crown.

(Firing, Sintering) Then a high temperature (1,400-1,550° C.) heat treatment was applied to the precursor crown 5' in a final sintering stage for desired strength.

(Applying caries inhibiting material) After the glazing, an etchant (ETCH-37, 37% phosphoric acid etchant with benzalkonium chloride, Bisco, USA) was applied on the open space area of the crown precursor for better adherence of the caries inhibiting material to the zirconia crown. Then caries inhibiting calcium releasing material 7 (TheraCal LC®, Bisco, USA) to stimulate hydroxyapatite growth was applied on each side of non-load bearing area of the mesial and distal open spaces.

(Curing) The calcium releasing material 7 applied on the precursor crown 5' was then light cured for polymerization.

(Finishing the mesial and/or distal surface) After polymerization, the surface of the applied caries inhibiting calcium releasing material was evenly adjusted by grinding with a dental hand wheel to match the contour of the rest of the final crown 5.

(Coating or polishing of the precursor crown) Then a coating or light-curing glazing material to replace the high temperature (over 800° C.) glazing process was applied evenly on the entire outside surface of the crown 5 for glazed effect. Commercially available VITA Enamic Glaze was used for coating purposes. This is a clear transparent light-curing varnish for surface sealing of restorations that requires polymerization. Following polymerization within a spectral range of 350-500 nm, this extremely thin liquid varnish provided a homogeneous and highly abrasion-resistant surface. Alternatively, the final crown 5 can be just hand polished if it does not go through the light curing and polymerization process.

Example 4

PFM, PFZ (Margin line) Margin line information of a cut tooth was received from the dentist before starting to make a crown. The crown margin line was created to cause the crown margin line and prepared tooth margin line to correspond with each other.

(Crown making with firing, option 1-2 and 2-2) A PFM (Porcelain Fused to Metal) or PFZ (Porcelain Fused to Zirconia) crown was made; substructures made of metal or zirconia were prepared and porcelain powders were build up to make the crowns. The first fire was done and another build up was carried out if necessary. A closed contact relationship was established as in option 1-2 of FIG. 6 so that the mesial and distal area can directly abut with the adjacent teeth. A high temperature (500-1,100° C.) heat treatment was applied to the precursor porcelain crown for desired strength. The unfinished crown had a buccal contour 14 (FIG. 6*b*) that is the same or substantially the same as that of the final crown 5 in FIG. 7*b*. Alternatively, the same process was done as above, except that the closed contact relationship was not established. Instead, a small open contact relationship was provided for the mesial and/or distal area so that more than enough of caries inhibiting material could be applied.

(Open space) Afterwards, an undercut on each of the non-load bearing mesial and distal areas was created by grinding away the ceramic body portion with a dental hand-piece, creating a hollow open space 9 and/or 10 as shown in FIG. 6*a*. After the completion of making the open space pit, the precursor crown 5' already had the same or substantially the same buccal contour 14 (FIG. 6*b*) as that of the final crown 5 as in FIG. 7*b*.

The open space can, alternatively, be made during build-up of porcelain powder; at least a small portion of the mesial and/or distal area can be left empty by not building up with porcelain powder. By carefully not filling the mesial and/or distal area with porcelain powder, an open space can be deliberately created to receive the second material of caries inhibiting material later on. Again, after the completion of making the open space pit, the precursor crown 5' has already had the same or substantially the same buccal contour 14 (FIG. 6*b*) as that of the final crown 5 as in FIG. 7*b*.

(Glazing) Then the outside of the precursor porcelain crown, except the open space, was glazed at a temperate of 500-1,100° C. for polished effect.

(Caries inhibition material) After the glazing, an etchant (ETCH-37, 37% phosphoric acid etchant with benzalkonium chloride, Bisco, USA) was applied on the open space area of the crown precursor for better adherence of the caries inhibiting fluoride releasing material to the porcelain or zirconia crown. Then a caries inhibiting fluoride releasing material 7 (KetacNano, 3M) was applied on each side of the non-load bearing area of mesial and distal open space 9 and/or 10.

(Curing) The material applied on the crown precursor was then light cured for polymerization.

(Finishing the contour) After polymerization, the surface of the applied caries inhibiting fluoride releasing material 7 was evenly adjusted by grinding with a dental hand wheel to match the contour of the rest of the final crown 5.

Example 5

CAD CAM Materials, Ultimate (Design of a restoration without or with an open space) Margin line information of a cut tooth was incorporated before starting to make a crown. A crown was then CAD (computer aided design) designed so that the mesial and distal area can abut with the adjacent teeth with a closed contact. Alternatively, a crown could be CAD (computer aided design) designed so that the non-load bearing mesial and/or distal area can have an open space away from the adjacent teeth, creating an open contact.

(Milling) Then this crown precursor was milled from a dental block using a CAD/CAM method. If the crown precursor has a closed contact relationship in association with the adjacent teeth, a small pit on each of the non-load bearing mesial and distal areas was additionally created by grinding away the ceramic body portion with a hand tool, creating a hollow open space 9 and/or 10 as shown in FIG. 6a. Currently available CAD/CAM blocks can be, but not limited to, Nano-Cera (B&D), Ultimate blocks (3M), Enamic, TriLux (Vita), eMax CAD (IvoClar). After the completion of making the open space pit, the precursor crown 5' already has the same or substantially the same buccal contour 14 (FIG. 6b) as that of the final crown 5 as in FIG. 7b.

(Heat processing) High temperature heat treatment is optional depending on the properties of the material. Generally, chair-side materials (Nanocera, Ultimate, Enamic, TriLux) that can be used directly by the dentists do not need high temperature post heat treatment, whereas materials used primarily by laboratories (e Max CAD) need high temperature (500-1,100° C.) heat treatment.

(Caries inhibiting material) Then an etchant (ETCH-37, 37% phosphoric acid etchant with benzalkonium chloride, Bisco, USA) was applied on the open space area of the precursor crown for better adherence of the caries inhibiting fluoride releasing material to the crown precursor. Then a caries inhibiting material (Vitrebond, 3M) was incorporated with 0.05 mL of silver nanoparticle colloidal solutions for added caries inhibiting effects. This material was applied on each side of the non-load bearing area of the mesial and distal open space.

(Curing) The material applied on the crown precursor was then light cured for polymerization.

(Finishing the contour) After polymerization, the surface of the applied fluoride releasing material was evenly adjusted by grinding with a dental hand wheel to match the contour of the rest of the final crown 5.

Although preferred embodiments of the invention have been described using specific terms, devices, and methods, such description are for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, and in part. Therefore, the spirit and scope of the appended claims should not be limited to the description of the preferred versions contained therein.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of making a dental crown or bridge restoration having occlusal, mesial side, buccal, distal side, and lingual walls, with the buccal wall configured to be adjacent a patient's cheek, and the lingual wall configured to be adjacent a patient's tongue, the occlusal wall configured to face an opposing tooth, the mesial and the distal side walls each configured to face a different adjacent tooth, and the walls being connected to define a concavity therein configured to receive and match a prepared tooth or an implant abutment, the method comprising, in sequence, the steps of:
   a) receiving a margin line information of the prepared tooth or the implant abutment; followed by
   b) forming a precursor crown or bridge restoration outside of a patient's mouth with a first restorative material, comprising creating a restoration margin line in the first restorative material corresponding with the margin line information of the prepared tooth or the implant abutment, creating a buccal contour on the buccal wall of the precursor crown substantially the same as or proportional to a desired final buccal contour on a final crown or bridge restoration, forming the concavity in the first restorative material outside of the patient's mouth to match the prepared tooth or the implant abutment, and creating an open space with an open space perimeter on or around at least one of the mesial side wall or the distal side wall with the open space separated from the concavity by the first restorative material; followed by
   c) filling and curing a second material, different from the first restorative material, inside the open space of the precursor crown or bridge restoration while outside the patient's mouth, defining the final crown or bridge restoration, and with the precursor crown or bridge restoration having a strength substantially equivalent to the final crown or bridge restoration, and with the buccal contour on the buccal wall being substantially the same as the buccal contour on the final crown or bridge restoration, prior to filling and curing the second material.

2. The method in accordance with claim 1, further comprising:
   filling the open space with the second material having a greater volume than a volume of the open space such that the second material extends outwardly beyond a surface of the mesial or the distal side walls of the precursor crown or bridge restoration.

3. The method in accordance with claim 1, further comprising:
   forming the precursor crown or bridge restoration adapted to have a closed contact relationship with a corresponding adjacent tooth when finished;

creating the open space adapted to have an open contact relationship with respect to the corresponding adjacent tooth due to the open space; and filling the open space with the second material adapted to have a closed contact relationship with the corresponding adjacent tooth when the crown or bridge restoration is installed on the prepared tooth or the implant abutment.

4. The method in accordance with claim 1, further comprising:

optionally heat hardening the precursor crown or bridge restoration if the first material does not have a strength substantially equivalent to the final crown or bridge restoration prior to filling and curing the second material inside the open space of the precursor crown or bridge restoration.

5. The method in accordance with claim 1, further comprising:

forming the precursor crown or bridge restoration from the first material that is pre-hardened and has a strength substantially equivalent to a final crown or bridge restoration.

6. The method in accordance with claim 1, further comprising:

heat hardening the precursor crown or bridge restoration, defining a hardened precursor crown or bridge restoration, prior to filling and curing the second material.

7. The method in accordance with claim 1, further comprising:

glazing, or polishing, or both, at least the buccal contour of the buccal wall of the precursor crown or bridge restoration, prior to filling and curing the second material.

8. The method in accordance with claim 1, wherein the open space comprises a pocket or a hole.

9. The method in accordance with claim 1, wherein the first material is inert, and the second material is bioactive.

10. The method in accordance with claim 1, wherein the first material has a higher flexural strength or a higher temperature tolerance than the second material.

11. The method in accordance with claim 1, wherein the first material comprises at least one of: dental porcelain, zirconia, glass ceramic, composite material, ceramic-composite hybrid material, resin composite, metal, CAD CAM restorative material, CAD CAM dental blocks; or combinations thereof.

12. The method in accordance with claim 1, wherein the second material comprises at least one of: calcium ions, phosphate ions, fluoride ions, titania ions, iodine, chlorhexidine, glass ionomer, resin-modified glass ionomer, compomers, calcium phosphate, tri-calcium phosphate (TCP), tetracalcium phosphate (TTCP), dicalcium phosphate anhydrous (DCPA), amorphous calcium phosphate (ACP), calcium and phosphate fillers that release calcium and phosphate ions, silver ions, nano silver particles, silver zeolite, or combinations thereof.

13. The method in accordance with claim 1, wherein creating an open space further comprises creating an undercut into the precursor crown or bridge restoration with a larger interior and a smaller opening thereto.

14. The method in accordance with claim 1, further comprising:

seating and securing the final crown or bridge restoration on the prepared tooth or implant abutment inside the patient's mouth; and with the second material adapted to have a closed contact relationship with the corresponding adjacent tooth.

15. The method in accordance with claim 14, wherein the open space perimeter is inside a contact area perimeter defined between the final crown or bridge restoration and the adjacent abutting tooth.

16. The method in accordance with claim 14, wherein the open space perimeter is outside and encompasses a contact area perimeter defined on the final crown or bridge restoration and adapted to contact the adjacent abutting tooth.

17. The method in accordance with claim 14, wherein the open space perimeter is partially inside and partially outside a contact area perimeter defined on the final crown or bridge restoration and adapted to contact the adjacent abutting tooth.

18. The method in accordance with claim 14, wherein the open space perimeter is completely outside a contact area perimeter defined on the final crown or bridge restoration and adapted to contact the adjacent abutting tooth.

19. A method for making a dental restoration configured to receive and match a prepared tooth or an implant abutment, the method comprising:

a) forming a precursor restoration from a first restorative material to have occlusal, mesial side, buccal, distal side, and lingual walls, with the buccal wall configured to be adjacent a patient's cheek, and the lingual wall configured to be adjacent a patient's tongue, the occlusal wall configured to face an opposing tooth, the mesial and the distal side walls each configured to face a different adjacent tooth;

b) forming a concavity in the first restorative material outside of a patient's mouth and opposite the occlusal wall and between the mesial side, buccal, lingual and distal side walls adapted to receive and match the prepared tooth or the implant abutment;

c) contouring the buccal wall to have substantially a desired final contour;

d) grinding or milling the first restorative material to form at least one open space in an exterior of at least one of the mesial side wall or the distal side wall with the open space separated from the concavity by the first restorative material;

e) heat hardening the precursor restoration defining a hardened precursor restoration;

f) disposing and securing a fluoride releasing material in the at least one open space of the hardened precursor restoration after heat hardening, defining a final restoration, the fluoride releasing material having an exposed exterior surface;

g) curing the fluoride releasing material while outside of a patient's mouth; and h) grinding the exposed exterior surface of the fluoride releasing material to match a contour of the final restoration.

20. A method for making a dental restoration configured to receive and match a prepared tooth or an implant abutment, the method comprising:

a) receiving a margin line information of the prepared tooth or the implant abutment;

b) forming a precursor restoration from a first restorative material outside of a patient's mouth to have occlusal, mesial side, buccal, distal side, and lingual walls, with the buccal wall configured to be adjacent a patient's cheek, and the lingual wall configured to be adjacent a patient's tongue, the occlusal wall configured to face an opposing tooth, the mesial and the distal side walls each configured to face a different adjacent tooth;

c) creating a restoration margin line in the first restorative material corresponding with the margin line information of the prepared tooth or the implant abutment;

d) forming a concavity in the first restorative material outside of the patient's mouth and opposite the occlusal wall and between the mesial side, buccal, lingual and distal side walls adapted to receive and match the prepared tooth or the implant abutment;
e) contouring the buccal wall to have substantially a desired final contour;
f) forming at least one open space in an exterior of at least one of the mesial side wall or the distal side wall with the open space separated from the concavity by the first restorative material, the open space adapted to have an open contact relationship, after heat hardening, with respect to a corresponding adjacent tooth due to the at least one open space;
g) heat hardening the precursor restoration defining a hardened precursor restoration;
h) disposing and curing a caries inhibiting material in the at least one open space of the hardened precursor restoration after heat hardening and while outside the patient's mouth, defining a final restoration, the caries inhibiting material having an exposed exterior surface, and with the first material having a higher temperature tolerance than the caries inhibiting material; and
i) seating and securing the final restoration on the prepared tooth or the implant abutment inside the patient's mouth, and with the caries inhibiting material adapted to have a closed contact relationship with the corresponding adjacent tooth.

21. A method for making a dental restoration configured to receive and match a prepared tooth or an implant abutment, the method comprising:
a) forming a precursor restoration from a first restorative material to have occlusal, mesial side, buccal, distal side, and lingual walls, with the buccal wall configured to be adjacent a patient's cheek, and the lingual wall configured to be adjacent a patient's tongue, the occlusal wall configured to face an opposing tooth, the mesial and distal side walls each configured to face a different adjacent tooth;
b) forming a concavity in the first restorative material opposite the occlusal wall and between the mesial side, buccal, lingual and distal side walls adapted to receive and match the prepared tooth or the implant abutment while outside a patient's mouth;
c) contouring the buccal wall to have substantially a desired final contour;
d) forming at least one open space in an exterior of at least one of the mesial side wall or the distal side wall with the open space separated from the concavity by the first restorative material;
e) optionally heat hardening the precursor restoration if the first material does not have a strength substantially equivalent to a final restoration; and
f) disposing and curing a caries inhibiting material in the at least one open space of the precursor restoration while outside of a patient's mouth, defining a final restoration, and with the precursor restoration having a desired contour on the buccal wall substantially the same as that of the final restoration, and with the concavity in the first restorative material adapted to contact the prepared tooth or the implant abutment when the final restoration is seated on the prepared tooth or the implant abutment inside the patient's mouth.

22. The method in accordance with claim 1, wherein filling and curing the second material further comprises:
grinding an exposed portion of the second material to match a contour of the final crown or bridge restoration.

23. The method in accordance with claim 1, wherein filling and curing the second material further comprises:
contouring an exposed portion of the second material to be flush with an exterior surface of the final crown or bridge restoration surrounding the second material.

24. The method in accordance with claim 1, wherein the second material comprises a caries inhibiting material.

25. The method in accordance with claim 1, wherein the second material comprises a fluoride releasing material.

26. The method in accordance with claim 20, wherein the carries inhibiting material comprises at least one of: calcium ions, phosphate ions, fluoride ions, titania ions, iodine, chlorhexidine, glass ionomer, resin-modified glass ionomer, compomers, calcium phosphate, tri-calcium phosphate (TCP), tetracalcium phosphate (TTCP), dicalcium phosphate anhydrous (DCPA), amorphous calcium phosphate (ACP), calcium and phosphate fillers that release calcium and phosphate ions, silver ions, nano silver particles, silver zeolite, or combinations thereof.

27. The method in accordance with claim 21, wherein the carries inhibiting material comprises at least one of: calcium ions, phosphate ions, fluoride ions, titania ions, iodine, chlorhexidine, glass ionomer, resin-modified glass ionomer, compomers, calcium phosphate, tri-calcium phosphate (TCP), tetracalcium phosphate (TTCP), dicalcium phosphate anhydrous (DCPA), amorphous calcium phosphate (ACP), calcium and phosphate fillers that release calcium and phosphate ions, silver ions, nano silver particles, silver zeolite, or combinations thereof.

28. The method in accordance with claim 1, wherein the concavity is a closed bore in the first restorative material, and wherein the concavity matches the prepared tooth or the implant abutment.

29. The method in accordance with claim 1, wherein the concavity in the first restorative material contacts the prepared tooth or the implant abutment when the final crown or bridge restoration is seated on the prepared tooth or the implant abutment.

30. The method in accordance with claim 1, wherein the open space has an open space perimeter entirely on the at least one of the mesial side wall or the distal side wall.

31. The method in accordance with claim 1, wherein the open space is bounded on all sides by the mesial side wall or the distal side wall.

32. The method in accordance with claim 1, wherein the open space is formed in the first restorative material by grinding or milling the first restorative material.

33. A method for making a dental restoration configured to receive and match a prepared tooth or an implant abutment, the method comprising:
a) forming a precursor crown or bridge restoration outside of a patient's mouth with a first restorative material, comprising creating a restoration margin line in the first restorative material corresponding with a margin line of the prepared tooth when cut to receive the dental restoration or the implant abutment and forming a concavity in the first restorative material to match the prepared tooth or implant abutment;
b) forming at least one open space in an exterior of a mesial side wall or a distal side wall of the precursor crown or bridge restoration with the open space separated from the concavity by the first restorative material;
c) optionally heat hardening the precursor crown or bridge restoration if the first restorative material does not have a strength substantially equivalent to a final restoration; and d) disposing and curing a caries inhibiting material in the at least one open space of the precursor crown or bridge restoration while outside of the patient's mouth, defining a final restoration, and with the precursor crown or bridge restoration having a desired contour on the buccal wall substantially the same as that of the final restoration.

* * * * *